(12) United States Patent
MacAulay et al.

(10) Patent No.: US 8,559,693 B2
(45) Date of Patent: Oct. 15, 2013

(54) SYSTEMS AND METHODS FOR AUTOMATED CHARACTERIZATION OF GENETIC HETEROGENEITY IN TISSUE SAMPLES

(75) Inventors: Calum Eric MacAulay, Vancouver (CA); Piotr Dubrowski, Vancouver (CA); Martial Guillaud, Gibsons (CA); Mehrnoush Khojasteh, Vancouver (CA)

(73) Assignees: British Columbia Cancer Agency Branch, Vancouver (CA); The University of British Columbia, Vancouver (CA)

( * ) Notice: Subject to any disclaimer, the term of this patent is extended or adjusted under 35 U.S.C. 154(b) by 840 days.

(21) Appl. No.: 12/682,667

(22) PCT Filed: Oct. 10, 2008

(86) PCT No.: PCT/CA2008/001817
§ 371 (c)(1),
(2), (4) Date: Apr. 12, 2010

(87) PCT Pub. No.: WO2009/046544
PCT Pub. Date: Apr. 16, 2009

(65) Prior Publication Data
US 2010/0290692 A1 Nov. 18, 2010

Related U.S. Application Data

(60) Provisional application No. 60/979,329, filed on Oct. 11, 2007.

(51) Int. Cl.
*G06K 9/00* (2006.01)
(52) U.S. Cl.
USPC .......................................... 382/133; 382/128

(58) Field of Classification Search
USPC ................................................... 382/128–133
See application file for complete search history.

(56) References Cited

U.S. PATENT DOCUMENTS 5,828,776 A * 10/1998 Lee et al. ....................... 382/133
8,116,551 B2 * 2/2012 Gallagher et al. ............. 382/133

(Continued)

FOREIGN PATENT DOCUMENTS

CA 2495411 A1 2/2004

OTHER PUBLICATIONS

Ishkanian, A., et al., "A tiling resolution DNA microarray with complete coverage of the human genome", Nature Genetics 36(3):299-303, 2004.

(Continued)

*Primary Examiner* — Neal Sereboff
*Assistant Examiner* — Anita Coupe
(74) *Attorney, Agent, or Firm* — Oyen Wiggs Green & Mutala LLP

(57) ABSTRACT

Systems and methods for the quantitative automated analysis of pathology samples identify groups of spatially-associated similar cells. Cells may be identified as belonging to a group on the basis of spatial location and biomarkers. In some embodiments the biomarkers are multicolour fluorescence in situ hybridization (FISH) signals. Characteristics of the cells in a group may be combined to provide quantitative FISH results that may compensate for variations and artefacts such as thin sectioning that can result in the loss of information due to damage. In heterogeneous tissue samples, grouping cells can permit quantitative results regarding pathological cells to be extracted despite the presences of infiltrating non pathological cells.

28 Claims, 12 Drawing Sheets

(56) References Cited

U.S. PATENT DOCUMENTS

| | | |
|---|---|---|
| 8,280,132 B2 * | 10/2012 | Madabhushi et al. ........ 382/128 |
| 2005/0265588 A1 | 12/2005 | Gholap et al. |
| 2006/0154236 A1 | 7/2006 | Altschuler et al. |

OTHER PUBLICATIONS

Chi, B., et al., "A software tool for the visualization of whole genome array comparative genomic hybridization data", BMC Bioinformatics 5:13, 2004.

Kim, M.K. et al., "Induction chemotherapy followed by concurrent chemoradiotherapy (CCRT) versus CCRT alone for unresectable stage III non-small cell lung cancer (NSCLC): randomized phase III trial",Journal of Thoracic Oncology, 12(8), 2007.

Chari, R., et al., "SIGMA: A System for Integrative Genomic Microarray Analysis of Cancer Genomes", BMC Genomics 7:324, 2006.

Theodosiou, Z., et al., "Automated Analysis of FISH and Immunohistochemistry Images: A Review", Cytometry Part A Published Online 71A:(7):439-450, 2007.

Liehr, T., et al., "Multicolor-FISH Approaches for the Characterization of Human Chromosomes in Clinical Genetics and Tumor Cytogenetics", Current Genomics 3:213-235, 2002.

Liehr, T. et al., "Multicolor FISH probe sets and their applications", Histol Histopathol 19(1):229-237, 2004.

Raimondo, F., et al., "Automated Evaluation of Her-2/neu Status in Breast Tissue From Fluorescent In Situ Hybridization Images", IEEE Transactions on Image Processing 14(9):1288-1299, 2005.

Cregger, M., et al., "Immunohistochemistry and Quantitative Analysis of Protein Expression", Arch Pathol Lab Med 130:1026-1030, 2006.

Emily, M., et al., "Spatial correlation of gene expression measures in tissue microarray core analysis", Journal of Theoretical Medicine 6(1):33-39, 2005.

Dubrowski, P., "An automated multicolour fluorescence in-situ hybridization workstation for the identification of clonally related cells", M.Sc Thesis, Department of Physics, University of British Columbia, (2008).

Epstein, L., et al., "Reutilization of Previously Hybridized Slides for Fluorescence In Situ Hybridization", Cytometry 21 (4):378-381, 1995.

Muller, S., et al., "Towards unlimited colors for Fluorescence in-situ hybridization (FISH)", Chromosome Research 10:223-232, 2002.

Walch, A., et al., "Sequential Multilocus Fluorescence In Situ Hybridization Can Detect Complex Patterns of Increased Gene Dosage at the Single Cell Level in Tissue Sections", Laboratory Investigation 81(10):1457-1459, 2001.

Levenson, R.M., "Spectral Imaging and Pathology: Seeing More", Laboratory Medicine 35(4):244-251, 2004.

Macaulay, C., et al., "Adaptive Color Basis Transformation, An Aid in Image Segmentation", Analytical and Quantitative Cytology and Histology 11(1):53-58, 1989.

Bilgin, C., et al., "Cell-Graph Mining for Breast Tissue Modeling and Classification", Conf. Proc. IEEE Eng. Med. Biol. Soc., 5311-5314, 2007.

Otsu, N., "A Threshold Selection Method from Gray-Level Histograms", IEEE Trans. Sys., Man., Cyber. 9: 62-66, 1979.

MacAulay, C. et al., "A Comparison of Some Quick and Simple Threshold Selection Methods for Stained Cells", Quick and Simple Threshold Methods 10(2):134-138, 1988.

MacAulay, C., et al., "An edge relocation segmentation algorithm", Anal Quant Cytol Histol 12(3):165-71, 1990.

McInerney, T. et al., "Deformable Models in Medical Image Analysis", IEEE Proceedings of MMBIA '96:171-180, 1996.

Ranefall, P., et al., "A new method for segmentation of colour images applied to immunohistochemically stained cell nuclei", Anal Cell Pathol 15(3):145-156, 1997.

Meyer, F., "Levelings, Image Simplification Filters for Segmentation", Journal of Mathematical Imaging and Vision 20 (1-2):59-72, 2004.

Wang, W.X., "Binary image segmentation of aggregates based on polygonal approximation and classification of concavities", Pattern Recognition, 31(10):1503-1524, 1998.

Meyer, F., "Iterative Image Transformations for an Automatic Screening of Cervical Smears", J Histochem Cytochem 27(1):128-135, 1979.

Ulam, S.M., "On Some Mathematical Problems Connected with Patterns of Growth of Figures", Appl. Math. 14:215-224, 1962.

Landini, G., et al., "Quantification of Local Architecture Changes Associated with Neoplastic Progression in Oral Epithelium using Graph Theory", Fractals in Biology and Medicine, vol. IV pp. 193-201, 2005.

Begg, C., et al., "Statistical Tests for Clonality", Biometrics 63:522-530, 2007.

Haroske, G., et al. "Cellular Sociology of Proliferating Tumor Cells in Invasive Ductal Breast Cancer", Analytical and Quantitative Cytology and Histology 18(3):191-8, 1996.

MacKinnon, N., et al., "Spectrally programmable light engine for in vitro or in vivo molecular imaging and spectroscopy", Appl Opt 44:2033-2040, Apr. 10, 2005.

MacKinnon, N., et al., "Hyperspectral imaging and spectral unmixing of stained tissue sections using a spectrally programmable light engine", Proc. SPIE 6441, Mar. 2007.

Fernandez-Gonzalez, R., et al., "A Tool for the Quantitative Spatial Analysis of Mammary Gland Epithelium", IEEE Transactions on Image Processing 14(9):1300-1313, Sep. 2005.

* cited by examiner

SYSTEMS AND METHODS FOR AUTOMATED CHARACTERIZATION OF GENETIC HETEROGENEITY IN TISSUE SAMPLES

CROSS-REFERENCE TO RELATED APPLICATION

This application claims priority from of U.S. patent application Ser. No. 60/979,329 filed on 11 Oct. 2007, which is hereby incorporated herein by reference.

For purposes of the United States of America this application claims the benefit under 35 U.S.C. §119 of U.S. patent application Ser. No. 60/979,329 filed on 11 Oct. 2007 which is hereby incorporated herein by reference.

FIELD OF THE INVENTION

The invention relates to the automated analysis of tissue samples. In some example embodiments, the invention is applied for the analysis of fluorescence in situ hybridization ("FISH") images, or images including immunohistochemistry ("IHC") biomarkers.

BACKGROUND

Cancer is a disease that involves changes in genetic and/or epigenetic structures which are transferable to subsequent generations of neoplastic progeny. Cancer cells gain a selective growth advantage over normal cells by accumulating specific genetic alterations. Many types of cancer involve multiple genetic alterations. The alterations typically occur in at least two groups of genes, protooncogenes and tumor suppressor genes. In many tumors the neoplastic process follows a multi-event genetic pathway involving the accumulation of an increasing number of genetic alterations. Specific patterns of genetic evolution have been associated with certain cancers and more aggressive neoplastic behavior.

Development of a neoplasia is thought to start with the clonal expansion of a single cell carrying an inheritable change in DNA that provides a growth/survival advantage. Any cell of this original clone may acquire additional inheritable changes, some of which could provide further survival advantages and give rise to more rapidly growing sub-clones.

Modern molecular technology has made it possible to identify many genetic alterations in human tissue. For example, techniques exist to detect the inactivation of both alleles of tumor-suppressor genes in human tumors. This could occur, for example through mutation of one allele and deletion of genetic material containing the other. Alteration of gene dosage (copy number alteration) of tumor-suppressor genes and protooncogenes are detectable across the entire genome through recent developments in genome-wide methodologies. Examples of these methodologies are described in:

Ishkanian A, et al., *A Tiling Resolution DNA Microarray with Complete Coverage of the Human Genome*. Nature Genetics 36(3):299-303, 2004. and Chi B, et al. *A software tool for the visualization of whole genome array CGH data*. BMC Bioinformatics 5:13, 2003.

Integrated analysis of genetic alterations and expression changes can be performed to identify genes that cause certain cancers. Examples of such integrated analysis are described in:

Lockwood W W et al., *Integrative genomic and gene expression analysis of NSCLC identifies subtype-specific signatures of pathway disruption*. IASLC 12th World Conf, Seoul Korea, Sep. 2-6, 2007; and Chari R, et al. SIGMA: *A System for Integrative Genomic Microarray Analysis of Cancer Genomes* BMC Genomics 7:324, 2006.

The ability to measure inheritable alterations across the entire genome of a lesion has resulted unprecedented amounts of data being available from individual cancers. Many have expounded that this expansive genetic information coupled with knowledge will lead to an era of effective personalized treatment, i.e. the detail with which one can interrogate the genetic building blocks of an individual cancer should lead to treatment specifically targeting the genetic events supporting the neoplastic tissue. However these genome-wide tests usually require 100 ng to 3,000 ng of DNA (10's of thousands to 1,000's of thousands of cells worth of material) to work reliably and are usually costly and labor intensive to perform.

Current genome-wide tests have the additional disadvantages that they can be insufficiently sensitive to detect some cancers. The clonal population of dangerous (leading to patient's mortality or morbidity) cells may be very few in number, below that detectible by existing genome-wide technologies, or may be masked by the surrounding non-lethal clones and infiltrating normal cells. Subdividing a lesion into subsets small enough that the DNA of a dangerous clonal population is no longer masked would result in too many genome wide analyses to be economically viable or practical. In addition, a frequent characteristic of developing lesions is genetic instability. Even if genome-wide test fails to identify a particular dangerous clonal population in a neoplasm, the dangerous clonal population may develop soon if precursor cells are present.

Genome-wide testing also fails to take into consideration genetic heterogeneity within tumors. The tissue making up individual tumors tends to be genetically heterogeneous. This occurs because of the mechanisms by which cancer cells grow and develop and also because invasive tumors almost always harbor some genetically normal cells intermixed to varying degrees with the tumor cells. Intra-tumor genetic heterogeneity has been reported in many types of cancers. The cells in a neoplasia that has reached the invasive stage are frequently genetically unstable and are prone to a high rate of mutation due to loss of check point effectiveness and loss of effective DNA repair mechanisms. Thus the genetic make up of cells and groups of clonally related cells can vary dramatically within an individual tumor.

Intra-tumor heterogeneity has important clinical implications. The extent of clonal heterogeneity can be an indicator of the lesion/patient current and future behavior.

IHC ('immunohistochemistry') and FISH ('fluorescence in situ hybridization') are methodologies which can be applied to detect gene copy number alteration (amplification and deletions) and altered gene expression/protein levels. IHC and FISH Are described, for example, in Theodosiou Z, et al. *Automated analysis of FISH and immunohistochemistry images*: A review. Cytometry Part A Published Online 71A: (7):439-450, 2007.

FISH involves hybridizing DNA probes to chromosomes. The DNA probes include components that fluoresce under appropriate illumination. Whether or not a chromosome within a cell includes a particular genetic sequence can be determined by observing whether or not a probe for the sequence has hybridized to the chromosome. FISH enables the detection, analysis, and quantification of specific numerical and structural characteristics within cell nuclei. FISH may be used to detect DNA deletions, translocations and amplifications. As such, FISH has application in studying genetic disorders, chromosomal abnormalities and characteristic underlying genetic features of tumors. Some applications of FISH involve the use of multiple probes that hybridize to different DNA sequences. The probes may fluoresce with different colors to facilitate distinction between them. Example techniques for multi-color FISH are described in:

Liehr T, et al. *Multicolor-FISH Approaches for the Characterization of Human Chromosomes in Clinical Genetics and Tumor Cytogenetics*, Current Genomics 3:213-235, 2002.

Liehr T et al. *Multicolor FISH probe sets and their applications*, Histol Histopathol 19(1):229-37, 2004.

FISH has proven to be as accurate as Southern blot analysis, while allowing the measurement of the fraction of altered cells and the heterogeneity within a given cell population.

One problem with FISH, especially where the tissue is in thin sections is that truncation artefacts can cause FISH signals which should be observed to be missing.

Immunohistochemistry ("IHC") is a technique that uses antibodies to stain proteins in situ. IHC allows the identification of cells with specific molecular phenotypes.

FISH or IHC results are typically evaluated in a semi-qualitative fashion by human observers. The reading of FISH images is a difficult task since manual dot scoring over a large number of nuclei and over different tissue samples is time consuming and fatiguing. Also, the results can be subjective and observer-dependent.

Raimondo F, et al. *Automated Evaluation of Her-2/neu Status in Breast Tissue From Fluorescent In Situ Hybridization Images*. IEEE Transactions on Image Processing 14(9): 1288-1299, 2005 describe a semi-automated system for analyzing FISH signals for the evaluation of Her-2/neu Status. The system uses image processing software to display the different color channels of a FISH image and apply thresholds for nuclei segmentation. However, the counting of dots in a semi-automatic manner remains impractical procedure for a pathologist, since it requires user intervention for excluding poorly segmented, overlapping, clustered or infiltrating non neoplastic cells. Quantitative analysis is usually done at the field level in which the number of cells with in the field is estimated and the amount of the marker (IHC or FISH spots) measured over the same field and an average score per cell calculated.

IHC biomarkers may be quantified by manual (visual) inspection, usually by a pathologist. Expression of IHC biomarkers is often scored on an ordinal 0-3 scale (in which 0=no staining, 1=weak staining, 2=moderate staining, and 3=strong staining). In some cases the scoring is combined with a scored interpretation of the markers' overall distribution. At best, manual inspection is semi-quantitative, reducing biomarker expression—which generally occurs in nature as a continuous, normal distribution to an ordinal scale. Visual inspection can also be confounded by the inherently subjective nature of human observation, affected by context (e.g. factors such as the amount of tumour present, background staining, and stromal staining). These issues can lead to undesirable inter- and intra-observer variability. In some cases, subtle sub-populations cannot be reliably identified using manual analysis.

The combination of IHC and computer-assisted image analysis systems provides the possibility of objective and reproducible quantification of the IHC staining. A first step in the quantitative analysis is imaging the field of view under a microscope. Different imaging modalities are currently in use, including three-color RGB cameras, monochrome cameras with specific wavelength filters, and multi-spectral imaging systems. Once the image of the field of view is captured, analysis of IHC images is performed, usually, in a semi-automated way with the aid of image analysis gene spatial software.

Commercially available image analysis software such as ACIS™, Ariol™ and Scanscope™ are reported to be able to successfully extract from images of IHC samples information such as average staining intensity within a region of interest and percentage of positive pixels. However, use of these systems typically requires significant operator intervention to set parameters such as thresholds for defining positive and negative areas. Although these software packages claim to perform cell-counting according to morphological and color criteria as well, it seems these features are not validated in published studies and are not typically used (see, for example, Cregger M, et al. *Immunohistochemistry and quantitative analysis of protein expression*. Arch Pathol Lab Med 130: 1026-1030, 2006).

Emily M, et al. *Spatial correlation of gene expression measures in tissue microarray core analysis*. Journal of Theoretical Medicine 6(1):33-39, 2005 measured the protein expression of DARPP-32 using IHC in a series of 31 patients from a series of 132 breast cancer patients to differentiate between patients which remained disease free after 5 years and those with recurrence or death within 5 years. They showed that a while a mean measure of the expression of DARPP-32 could detect the bad prognosis patients 83% of the time it did so with a poor specificity of 44%. This is in contrast with a specific cell-by-cell spatial correlation measure which demonstrated the same detection rate of 83% while maintaining a specificity of 76%.

There remains a need for practical semi-automated and automated methods and apparatus capable of providing information about tumors and other neoplastic tissues.

Tumor growth, prognosis, and metastasis are dependent on multiple interactions of tumor cells with homeostatic factors in the micro-environment of the neoplasia within the host. Examples of factors that correlate to outcomes include:

tumor aneuploidy (which is strongly associated with poor outcomes).
  specific genetic alterations, such as p53 deletion, cMYC amplification, EFGR amplification, etc.
  expressions of estrogen and progesterone.
  etc.

There remains a need for methods and apparatus that can identify genetic and molecular signatures/profiles identifying even small populations of dangerous cells across entire lesions in a high throughput fashion without excessive false positives.

SUMMARY OF THE INVENTION

This invention has a number of different aspects. One aspect provides systems and methods for the quantitative analysis of multicolor FISH signals. Such systems and methods may be applied to provide quantitative analyses of multicolor FISH signals in pathological specimens such as tumor biopsies. Such analyses may be utilized, for example, for things such as:

testing for residual disease after treatment of cancer.
  testing for fetal chromosomal abnormalities.
  assessing likely outcomes for cancer treatments.
  determining tumor characteristics.
  identifying tumors which will have resistance to chemotherapy (for example resistance to cis-platinum/vinorelbine chemotherapy).

Another aspect provides methods and systems for automated scanning of excised tissues in order to identify clonal subpopulations with specific DNA amplification and DNA deletion profiles. Identification of such clonal subpopulations may be applied for identification of tumor subpopulations with specific characteristics relevant to predicting patient response to chemotherapy (for example tumor subpopulations that may be resistant to certain chemotherapy or other treatment regimes).

Another aspect provides methods for automated identification and quantification of FISH signals in clonal subpopulations of cells in images using image analysis techniques.

Another aspect provides methods for automated determination of tissue characteristics comprising obtaining an image of a tissue sample. The image depicts cell nuclei and corresponding biomarkers in the tissue sample. The method processes the image to identify in the image: the cell nuclei, corresponding biomarkers associated with the cell nuclei, and spatially-connected groups of the cell nuclei. The method computes characters of the spatially-connected groups of cell nuclei and, based at least in part on the computed characters, highlights regions corresponding to the spatially-connected groups of cell nuclei.

Another aspect provides methods for automated determination of tissue characteristics that comprise obtaining an image of a tissue sample, the image depicting cell nuclei and corresponding biomarkers in the tissue sample; processing the image to identify the cell nuclei and corresponding biomarkers in the image and to identify spatially-connected groups of the cell nuclei in the image; and computing characters of the spatially-connected groups of cell nuclei. Identifying spatially-connected groups of the cell nuclei in the image comprises: identifying a selected set of the cell nuclei for which the corresponding biomarkers satisfy a selection criterion; establishing a network of cell-to-cell connections connecting adjacent ones of the cell nuclei; and identifying a group of the cell nuclei of the selected set that are all interconnected by at least one chain of the cell-to-cell connections wherein: the at least one chain passes only through cells of the selected set except for in at least one gap in which the chain passes through from 1 to n consecutive cells that are not in the selected set and at least one pair of cells in the group is not interconnected by any chain of the cell-to-cell connections that passes only through cells of the selected set. A character may be computed for the group of cells or for one or more cells of the group.

Another aspect provides apparatus for automated or semi-automated analysis of images of tissues having features, combinations of features or sub combinations of features as described herein.

Another aspect provides computer program products useful for the automated or semi-automated analysis of images of tissues having features, combinations of features or sub combinations of features as described herein.

Some aspects of the invention are described in Dubrowski, Piotr, *An automated multicolour fluorescence in situ hybridization workstation for the identification of clonally related cells*, M. Sc Thesis, Department of Physics, University of British Columbia, (2008) which is hereby incorporated herein by reference.

Further aspects of the invention and features of specific embodiments of the invention are described below. The following drawings, descriptions and examples are illustrative in nature and not restrictive.

BRIEF DESCRIPTION OF THE DRAWINGS

The accompanying drawings illustrate non-limiting example embodiments of the invention.

DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

Figure 1:
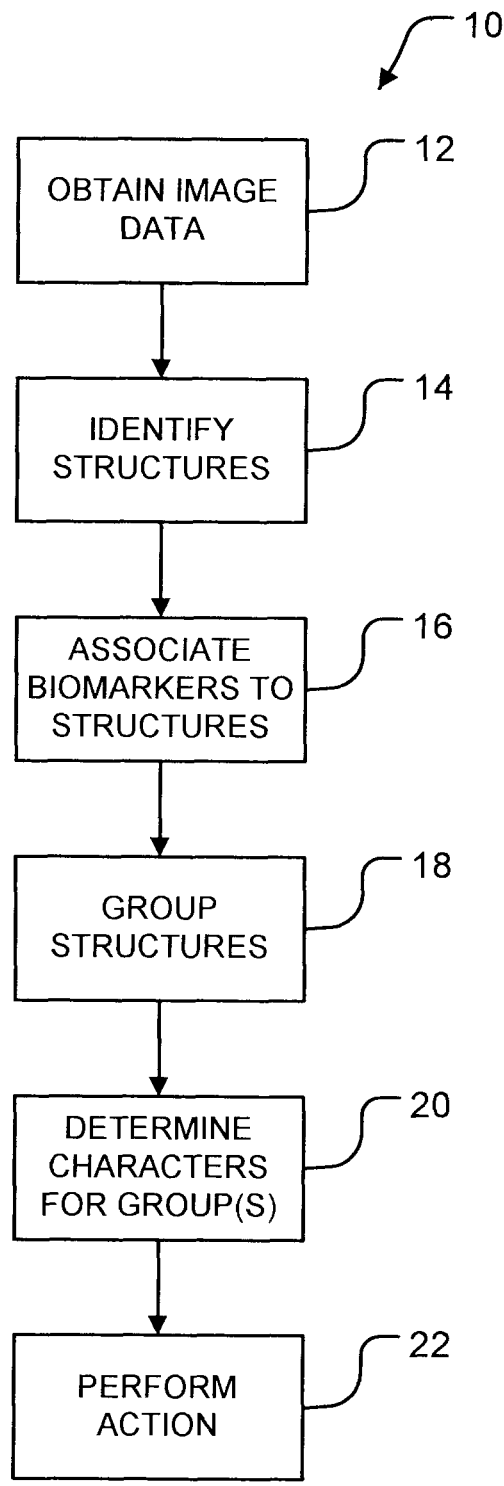
FIG. 1 is a flow chart illustrating a method for characterizing tissue according to an example embodiment of the invention.

FIG. 1 illustrates a method 10 for characterizing tissues according to an example embodiment of the invention. Block 12 involves obtaining one or more images of a tissue using an imaging modality capable of detecting biomarkers in the imaged tissue. Block 12 may comprise obtaining an image of a tissue sample that has been treated with a probe, stain, or other treatment to reveal biomarkers at the cellular level. In some embodiments, block 12 comprises obtaining multiple images of the same tissue. The multiple images may be taken using different imaging modalities, different illumination conditions or after applying different stains or other probes to the tissue sample. The multiple images may be taken at different focus settings to preserve information about the three-dimensional structure of thicker tissue sections. Obtaining an image may comprise retrieving one or more previously-stored images of a tissue sample. The images obtained in block 12 may depict a very large number of cells for which it would be completely impractical for a human observer to manually make observations of the types described herein, especially on a high throughput basis. For example, the images may depict more than $10^5$ cells in some cases.

The tissue sample is prepared suitably for the imaging modality to be used. For example, the tissue sample may be formalin-fixed, embedded in paraffin, sectioned and imaged with a microscopic imaging system. In non-limiting example embodiments the sections are about 5 μm to 10 μm thick.

In some embodiments, a tissue sample is hybridized with a first set of one or more probes and imaged and then hybridized with another set of one or more probes and imaged again. This may be repeated for more probes. Such techniques permits analysis of the same tissue sample with a large number of probes. Techniques for the reuse of previously hybridized slides are described, for example, in Epstein L, et al. *Reutilization of previously hybridized slides for fluorescence in situ hybridization*, Cytometry 21(4): 378-381, 1995.

Muller S, et al. *Towards unlimited colors for Fluorescence in-situ hybridization (FISH)*, Chromosome Research 10:223-232, 2002.

Walch A, et al. *Sequential Multilocus Fluorescence In Situ Hybridization Can Detect Complex Patterns of Increased Gene Dosage at the Single Cell Level in Tissue Sections*, Laboratory Investigation 81(10):1457-1459, 2001.

The inventors have applied probes to cells in individual metaphases and have demonstrated that rehybridization of interphase cells can be performed both on individual cells and on formalin fixed parafin-embedded tissues.

A specific set of FISH probes may be constructed to detect a particular trait. Such probes may be created starting from tissue samples with known CGH ("Comparative Genomic Hybridisation") profiles and biological behaviour (e.g. response to certain therapy or drug resistance). A set of clones which are significantly altered (e.g. by genetic deletions or amplifications) is detected in the tissues. These clones can then be synthesized into FISH probes using a variety of fluorescence markers such as: DEAC, SpectrumAqua, SpectrumGreen, SpectrumGold, Cy3, SpectrumOrange, Texas-Red, SpectrumRed, and Cy5.

One example procedure for making FISH probes is to obtain samples containing clonal DNA which has been previously amplified e.g. through one round of Degenerate Oligonucleotid Primer (DOP) PCR, concentrated and frozen. The samples are thawed, set through another round of DOP-PCR and subsequently purified. Once enough product is amplified, the DNA is labelled with fluorescent (for direct) or haptene (for indirect) nucleotides via a Klenow reaction. The reaction is carried out in proper amounts of three unlabeled nucleotides and a deficit of the competing unlabelled nucleotide in order to force the incorporation of the labelled nucleotide base. Upon completion, any unincorporated fluorophore is removed, for example via ethanol precipitation or simple concentration/purification kit. The final probe is re-suspended in hybridization buffer and is ready for use.

A second example procedure for making FISH probes involves the use of Bacterial Artificial Chromosomes (BACs) grown in *E. coli* hosts. BACs of interest are grown overnight in media containing an antibiotic to ensure only the specific *E. coli* survive and are cultured the next day. Once the BAC DNA is isolated, a Nick Translation reaction is used to label the DNA with either fluorophore (for direct) or haptene (for indirect) conjugated nucleotide. This reaction is also carried out with a deficit of competitive unlabelled nucleotide base. The finished reaction can then be ethanol precipitated and resuspended in hybridization buffer ready for use.

The first example procedure above is simpler than the second procedure but can produce a relatively high background signal. The second example procedure has been found to yield good results with lower background staining and larger, brighter signals. The quality of a FISH probe may be checked using a NanoDrop absorption spectrometer to verify the concentration of DNA in the probe and the proportion of fluorophore incorporation. Probes with incorporations higher then about 10 pmol/μl gave consistently good results once hybridized. Once the incorporation of a probe is deemed sufficient, probes are hybridized to normal human metaphase spreads to evaluate the specificity of the probes. FISH probes may also be made using other suitable processes.

IHC biomarkers in tissue sections can be imaged in fluorescence and/or absorption. In embodiments which use staining by multiple IHC stains as biomarkers then imaging may comprise multi-spectral imaging techniques. An example of such techniques is described in Levenson R M, *Spectral Imaging and Pathology: Seeing More*, Laboratory Medicine 35(4):244-251, 2004.

In some embodiments, the biomarkers comprise both IHC and FISH biomarkers. In such embodiments:
  if the IHC and FISH probes are compatible then they may be applied to the same prepared tissue section either at the same time or sequentially;
  IHC and FISH probes may be applied separately to two adjacent sections and images of those sections or results based on images of those adjacent sections may be subsequently combined. In some embodiments a suitable non-linear spatial transformation is applied to the image of at least one of the sections so that the images of the two adjacent sections are aligned to within a cell diameter for all cells in the sections.

Block 14 involves applying image recognition techniques to recognize structures in the image or images obtained in block 12. Block 14 may comprise identifying cell boundaries using image analysis techniques such as edge location and segmentation. The structures recognized in block 14 include biomarkers together with cells and/or intracellular structures such as cell nuclei.

Where the biomarkers comprise FISH signals or other similar signals then detecting the biomarkers may comprise image processing steps such as spatial filtering to remove slowly varying background while preserving spots (local background variation from inhomogeneous staining). This may be done, for example, by applying a top-hat transform or other feature-extraction transform. FISH spots can be recognized as areas of local maxima that satisfy suitable size and/or intensity thresholds. For example, a spot may be recognized as a FISH spot if it has an area>2 pixels and an intensity level of at least some suitable threshold.

In block 16, biomarkers recognized in block 14 are associated with other structures recognized in block 14. For example in some embodiments:
  block 16 comprises associating one or more fluorescent spots from FISH with individual cells or cell nuclei in which those fluorescent spots are observed. In some embodiments the fluorescent spots are from multi-color FISH.

In other embodiments block 16 comprises associating IHC spots or staining density, morphological features of cells, or other biomarkers with cells and/or cell nuclei. In some embodiments block 16 comprising associating biomarkers of two or more different types with cells or cell nuclei.

Further processing, as described in the following text, may be applied essentially independently of the specifics of tissue preparation, the modality or modalities by which images are acquired, and the techniques applied to segment the images to identify cells, cell nuclei, biomarkers or other structures depicted in the images.

Block 18 comprises identifying groupings of the structures (e.g. groupings of cells or cell nuclei) recognized in block 16. The groupings may be made based on rules applied to factors such as:

Spatial relationships between structures: Some examples of spatial relationships between different structures are the distance separating the structures and whether or not the structures are members of higher-order structures within the image. The higher-order structures may be defined with reference to mathematical constructs. In some embodiments distance is expressed in terms of the degree to which different structures are nearest-neighbours. For example, rules may specify grouping nearest neighbours together or first- and second-nearest neighbours together or first- to $n^{th}$-nearest neighbours together. Higher-order structures may comprise chains, clusters or other spatial groupings of cells, for example. Whether or not a particular cell or other structure is a member of a higher-order structure can be expressed in terms of a rule or mathematical construct defining the higher-order structure.

Biomarkers associated with the structures: For example, a rule may group together cells that share a defined pattern of biomarkers as well as having a defined spatial relationship. The biomarkers may be of one type (e.g. all FISH spots or IHC spots) or may include biomarkers of heterogeneous types.

In some embodiments, block 18 comprises establishing mathematical constructs to define neighboring cells and extended cell neighborhoods. This may comprise, for example applying Voronoi tessellation or Delaunay triangulation. Other methods known to those skilled in the art may also be used.

In block 20 characters are determined for at least some of the groups identified in block 18. The characters may comprise, for example:

binary values indicating whether or not a specified group has a particular property or combination of properties. The property or combination of properties may me specified by a rule;

values from a specified set. Which value is attributed to a group may be determined by applying one or more rules to one or more properties of the group;

scores or other values that can vary continuously over some defined range;

vector quantities having values determined by properties of the group or its member structures;

combinations of one or more of the above;

etc.

In some embodiments the character is determined for each cell or cell nucleus in an image (each cell or nucleus is a member of a group—a cell or nucleus not associated with any other cells or nuclei can be considered to be a member of a group that has only one member). In some embodiments the character is a function at least in part of the number of members in a group. In some embodiments, the character is a function of the spatial relationship of a cell, nucleus or other structure to any remaining members of the group to which the cell, nucleus or other structure belongs.

In block 22 an action is performed. The action applies the characters determined in block 20. The action may, for example, comprise one or more of:

creating an image wherein intensity values, colors, highlighting or the like is determined at least in part by the characters determined in block 20. The image may be displayed for viewing/analysis by a human observer and/or saved for future analysis or display;

Based at least in part on characteristics associated with one or more groups of cells in the regions, selecting one or more sub-regions of the image to be: enlarged, saved for future analysis, subjected to further automated analysis, displayed, and/or the like.

Determining whether the characters satisfy a condition indicating the need for special handling or some further action.

The action results in an image or other data that preserves local information regarding different groups of cells identified in block 18. The action may additionally compute an overall score or other index that provides information regarding some property of the imaged sample as a whole.

EXAMPLE

Figure 2:
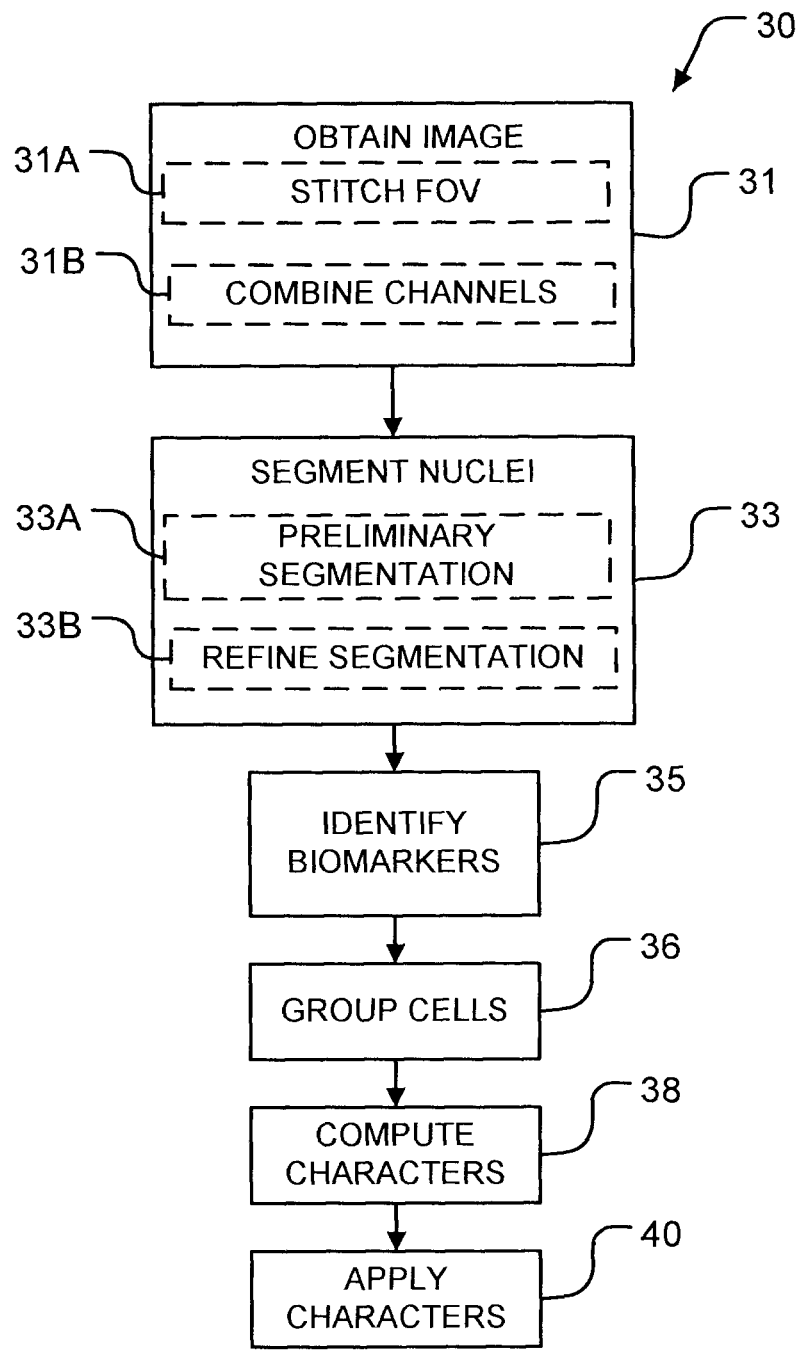
FIG. 2 is a flow chart which illustrates a method according to a more detailed example embodiment.

The following describes an example embodiment of the invention. A method 30 according to this example embodiment is illustrated in FIG. 2. An image is obtained in block 31. Obtaining the image may comprise stitching together two or more fields of view to provide an image that covers an entire region of interest as indicated in block 31A. If this is done then it should be done in a way that correctly aligns the separate fields of view in the composite stitched image.

Some imaging modalities produce images made up of more than one channel. The number of channels depends on the imaging modality used to obtain the image. For example, depending upon the spectral characteristics of the objects to be analysed, as well as the spectral characteristics and number of any stains used, imaging modalities such as RGB, Hyper-spectral, narrowband wavelength specific filters, etc. may be used. In the case of IHC, a conventional RGB camera may provide enough contrast to identify cell nuclei stained with a marker like Ki67, which is specific to cell nuclei. For markers like p16 that are not specific to cell nuclei, hyper-spectral imaging may provide improved contrast.

In the example embodiment, information from all channels of the image data are combined into one gray-scale image as indicated in block 31B. Alternative embodiments that apply segmentation methods that work on vector-valued pixels may not require multiple channels to be combined.

Where two or more channels are combined into one image, the combination is performed in a manner that enhances contrast between objects to be distinguished. Some techniques that may be applied to combining channels in block 31B include:

Principal Component Analysis (a class of methods that obtain a linear combination of the image channels that contains the maximum amount of information). Principal component analysis is described, for example, in MacAulay C, et al. *Adaptive color basis transformation, an aid in image segmentation*, Anal Quant Cytol and Histol 11(1):53-58, 1989.

Linear Discriminant Analysis (a class of methods that determine a linear combination of image channels that best separates two different classes of pixels based on a training set).

Spectral Unmixing (a class of methods also called 'Linear Decomposition' that separate the spectrum of each pixel of an image into spectra of its components).

For example one can perform a least-squares best fit approximation to determine how much of each individual component spectrum would be required to most accurately recreate the measured signal spectrum. Linear spectral decomposition assumes that the spectrum observed for each pixel is made up of a linear combination of pure spectral components. The linear combination methods can be applied in situations where pure spectra combine linearly or nearly linearly. This property holds for fluorescence images. Transmission images are advantageously converted to optical density before applying the linear combinations algorithm.

Figure 3A:
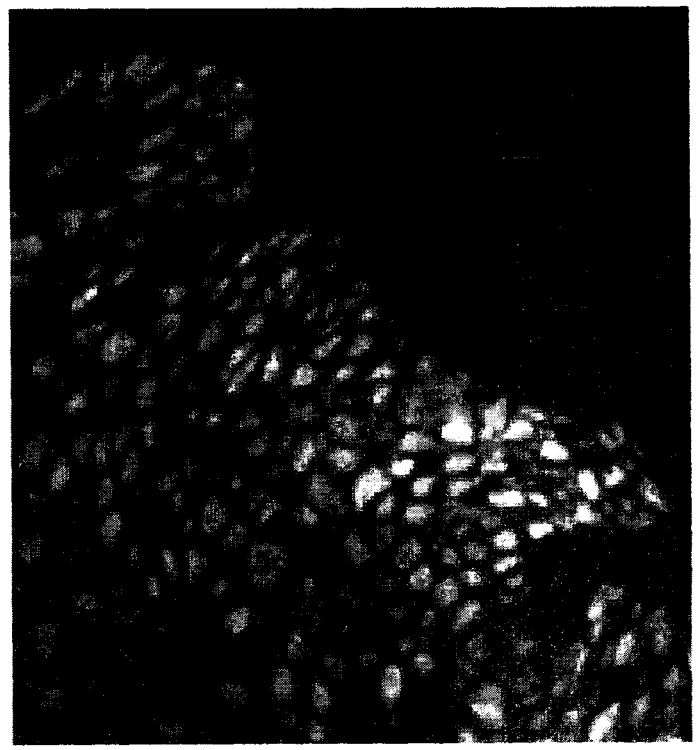
FIGS. 3A and 3B are images showing the contributions of Haematoxylin and DAB to the spectrum of a hyperspectral absorption image.
Figure 3B:

As an example involving the acquisition of narrowband images and the application of spectral unmixing, a sample was illuminated with light having narrow-band spectral profiles with a bandwidth of 15 nm generated by a programmable light engine (SPLE). A series of hyperspectral absorption images of DAB- and Hematxylin-stained tissue sections from cervical biopsies was acquired. The central wavelength of the illuminating light was varied from 415 nm to 685 nm to obtain a stack of images of each tissue section taken with different wavelengths of illuminating light. The stacks of images were analysed using custom MATLAB™ software configured to unmix the contributions to the intensity of each pixel of each of Haematoxylin and DAB. The results are shown in FIGS. 3A and 3B.

After an image (or images) of a suitably-prepared tissue sample is obtained the image is processed to segment the nuclei of cells depicted in the image as indicated by block 33. Segmentation involves separating the depicted nuclei from both the background and from other nuclei. Segmentation of the nuclei in histological images of tissues can be complicated by the existence of touching and overlapping nuclei, different shapes, sizes, and colors of nuclei, and non-uniform background caused by other tissue compartments such as cytoplasm and membrane, and by non-specific staining. To achieve good segmentation of structures in an image, the segmentation may be performed in a preliminary step 33A and a refinement step 33B. A range of suitable segmentation algorithms are described in the literature and known to those of skill in the art. The particular method used to achieve segmentation is not critical. The invention is not limited to the following examples of segmentation methodologies.

In the illustrated embodiment, preliminary step 33A may, for example, comprise applying automated thresholding techniques to perform a preliminary separation of objects from background. The result of the preliminary separation may comprise a mask that can be refined later. Preliminary separation may comprise, for example, performing one or more of:

Otsu thresholding as described, for example, in Gonzalez R C et al., *Digital Image Processing*, Prentice Hall, 2002, and N. Otsu *A threshold selection method from gray-level histograms*. IEEE Trans. Sys., Man., Cyber. 9: 62-66 (1979).

locally adaptive Otsu thresholding, and histogram analysis techniques as described, for example, in MacAulay C et al., *A comparison of some quick and simple threshold selection methods for stained cells*, Anal Quant Cytol Histol 10(2):134-138, 1988.

The preliminary separation may fail to properly separate touching and overlapping objects. The preliminary separation may be refined, as indicated by block 33B, to, inter alia, separate touching and overlapping objects. The refinement may make use of a range of available information in the image including grey levels, gradient and edge information and shape information. In an example embodiment, refinement of the preliminary separation comprises applying an iterative sequence of edge-based and shape-based methods until quality control features extracted for each segmented object indicate that the object can no longer be split and the edges are optimally positioned. These quality control features describe the shape of the objects and may be found through stepwise linear discriminant analysis on a training set of objects pooled over several images.

Suitable edge-based methods include the edge relocation algorithm described in MacAulay et al. *An edge relocation segmentation algorithm*, Anal Quant Cytol Histol 12(3):165-71, 1990 and active contour models as described in McInerney T et al., *Deformable models in medical image analysis*: a survey, Medical Image Analysis 1(2):91-108, 1996.

Suitable shape-based methods include watershed segmentation performed on the distance transform of the mask of the objects as described in Ranefall P, et al. *A new method for segmentation of colour images applied to immunohistochemically stained cell nuclei*, Anal Cell Pathol 15(3):145-156, 1997 and marker-based watershed as described in Meyer F, *Levelings, image simplification filters for segmentation*, J of Mathematical Imaging and Vision 20(1-2):59-72, 2004, and other algorithms for segmentation of aggregates based on the position of concavities, for example as described in Wang W X, *Binary image segmentation of aggregates based on polygonal approximation and classification of concavities*, Pattern Recognition, 31(10):1503-1524, 1998.

Block 35 identifies biomarkers in the image. This block may include image processing steps. For example, for FISH spot detection the top-hat transform may be applied to isolate spots form slowly varying background staining. The top-hat transform may be followed by thresholding or maxima detection to find spot locations and areas. This technique is described, for example in Meyer F *Iterative image transformations for an automatic screening of cervical cancer*, J Histochem Cytochem 27(1):128-135, 1979. Each of the biomarkers is associated with a cell or cell nucleus.

Block 36 identifies groups of cells. The association of cells into groups (which may be called 'clonal neighbourhoods') may be done in a manner that avoids or reduces artefacts which result when the image depicts cells affected by sectioning artefacts (sectioning artefacts may include, for example, FISH spot count variability and clonal connectivity by cells above or below the section imaged). This may be done through a flexible definition of a clonal neighbourhood. Block 36 may comprise applying a mathematical structure to quantify cell-to-cell spatial associations. In some embodiments the mathematical structure includes one or more of a Delaunay graph, Voronoi neighbourhoods and local trees such as Ulam trees. Ulam trees are described, for example, in:

Ulam, S. M., *On Some Mathematical Problems Connected with Patterns of Growth of Figures*, Appl. Math. 14, 215-224 (1962); and A. W. Burks (ed.), *Cellular Automata*, Univ. of Illinois Press, Urbana, 1970, pp. 219-231.

In some embodiments the groups of cells are defined geometrically. Preferably the groups of cells are defined based upon both geometrical rules and cell traits, as indicated by biomarkers detected in block 35.

The criteria that biomarkers, for example FISH spots, should satisfy for a cell to be considered 'positive' and potentially included in a group may be established with reference to the approach described in C. Begg et al. *Statistical Tests for Clonality*, Biometrics 63:522-530, 2007. Such techniques can assist in defining how many of which FISH probes should be observed for a cell to be considered to have the biologically relevant genomic alteration profile being studied. Techniques similar to those described in C. Begg et al. may also be applied to determine the likelihood that adjacent (or distal) clonal groups of cells are closely related genetically or are distantly related, giving a measure of heterogeneity within the lesion being imaged. For IHC analysis the mathematical constructs defining cell clusters may be based upon the clonal expansion of modified clones in neoplastic development models such that the mathematical constructs result in cell clusters that are likely to have biological significance.

Sectioning tissue samples can cause cell nuclei to be truncated. Truncation is a particular issue when the sections are thin. For example, it is common to prepare tissues in 5 μm thick sections. Cell nuclei can have average diameters greater than this. Truncation artefacts are a particular issue in processing FISH biomarkers since truncation can cause FISH spots to be absent.

In some embodiments, truncated cells (i.e. cells affected by sectioning artefacts) are recognized as such. This may be done, for example, by considering nuclei having an area or diameter that is less than some threshold (e.g. having a diameter less than one half the diameter of the average cancer cell nucleus) to be truncated.

In some embodiments, whether a cell is considered to be positive for a trait is determined solely from the biomarkers associated with that cell. For example, a rule may specify that a cell should be considered positive if certain specific FISH spots are associated with the cell and not otherwise.

Figure 10:
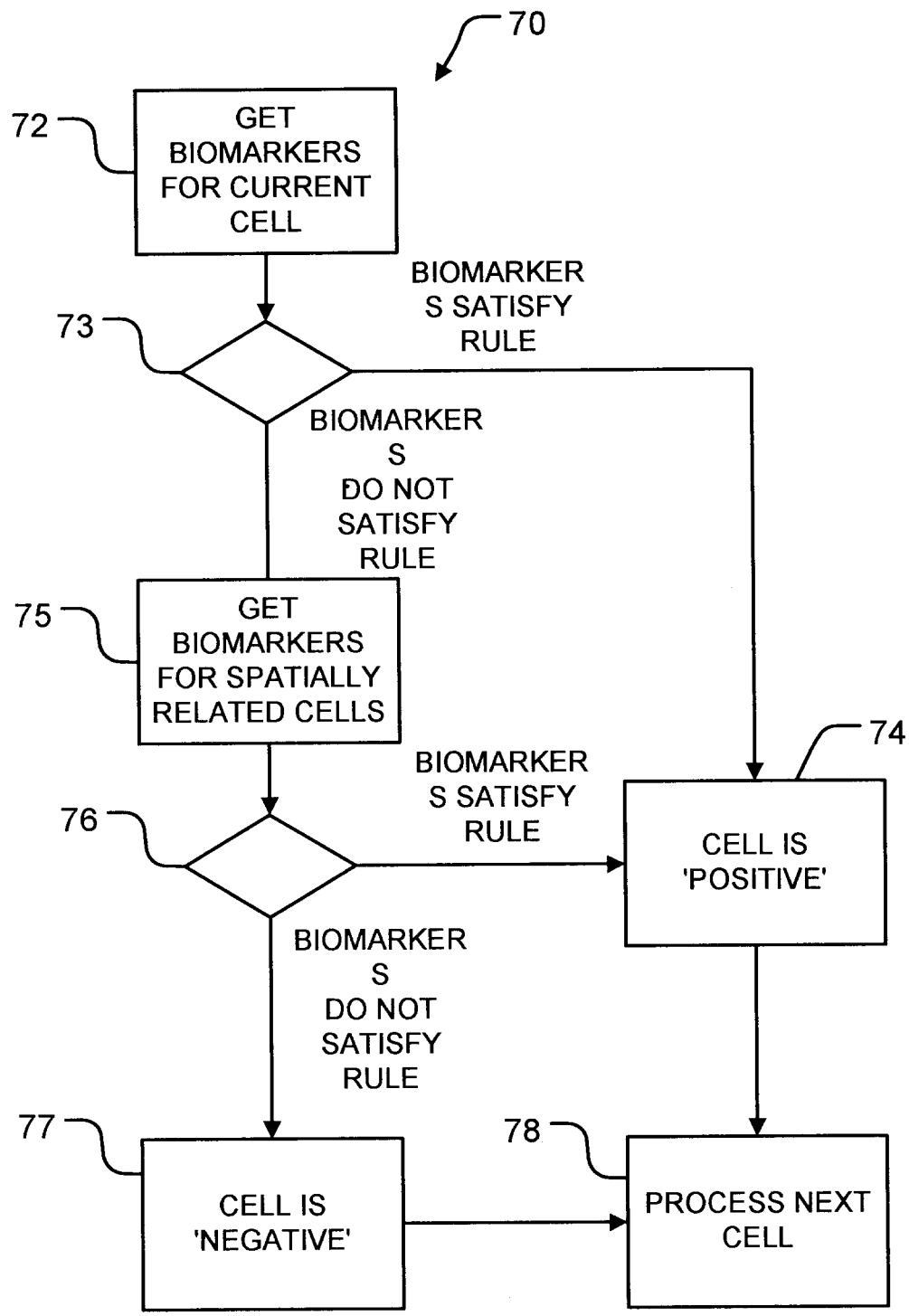
FIG. 10 is a flow chart illustrating a method for determining whether to consider a cell as being positive for a trait.

In other embodiments, whether a cell is considered positive for a trait is determined with reference to biomarkers of the cell and surrounding cells. Method 70 of FIG. 10 is an example. In block 72 the biomarkers for a current cell are received. In block 73, the biomarkers are tested in a rule. If the biomarkers satisfy the first rule then the cell is positive. Otherwise, processing continues at block 75. Block 75 retrieves biomarkers for cells that are spatially related to the current cell. For example, block 75 may retrieve biomarkers for cells in a Voronoi neighborhood surrounding the current cell.

In block 76 the biomarkers retrieved in block 75 are tested against a second rule. The second rule sets conditions for biomarkers associated with the spatially related cells being considered. If the biomarkers of the spatially-related cells satisfy the second rule then the current cell is identified as being positive in block 74 otherwise the current cell is identified as being negative in block 77. At block 78 method 70 proceeds to process the next cell.

Many modifications of method 70 are possible. For example, if block 73 determines that the current cell comes very far from satisfying the rule then the current cell may be marked as being 'negative' without considering biomarkers for spatially-related cells. As another modification of method 70, blocks 72 and 73 may be omitted and the determination as to whether the current cell is positive may be made based on the biomarkers of the spatially related cells (including the current cell).

As a specific example of the application of method 70, consider the case where the first rule requires the cell to have a specific set of four FISH spots as biomarkers. If the cell has all four of the FISH spots then the cell is identified as being positive in block 73. Otherwise biomarkers are retrieved for neighboring cells. The second rule may specify that the cell will be considered positive if: for each of the four FISH spots at least a first threshold percentage of the neighboring cells have the FISH spot. In some cases the second rule may also require that at least a second threshold percentage of the neighboring cells have a specified number (e.g. 2, 3 or 4) of the four spots. In some cases the second rule may require that the current cell itself must have at least some number (e.g. 1, 2 or 3) of the four FISH spots.

After a set of cells have been identified as being 'positive' for some trait (meaning that their biomarkers or the biomarkers of adjacent cells satisfy some rule or rules) then the spatial relationships of the positive cells may be studied.

Figure 4A:
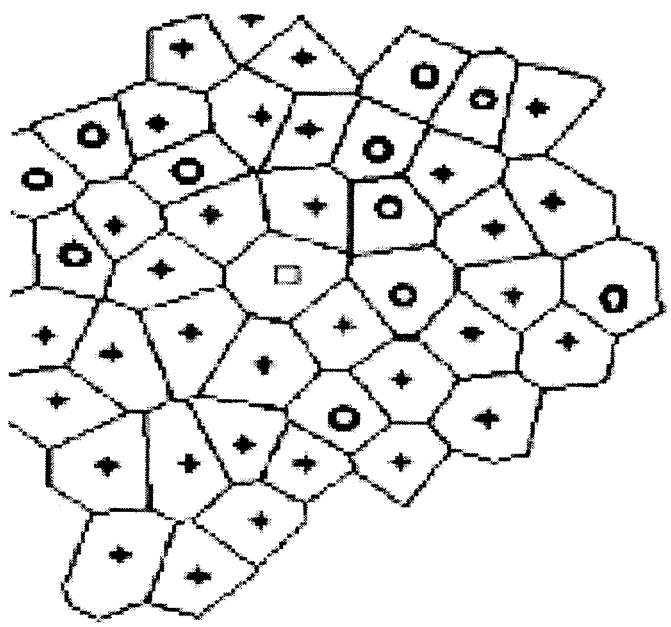
FIG. 4A is an example of a Voronoi tessellation applied to an image in which a number of cell nuclei have been identified.
Figure 4B:
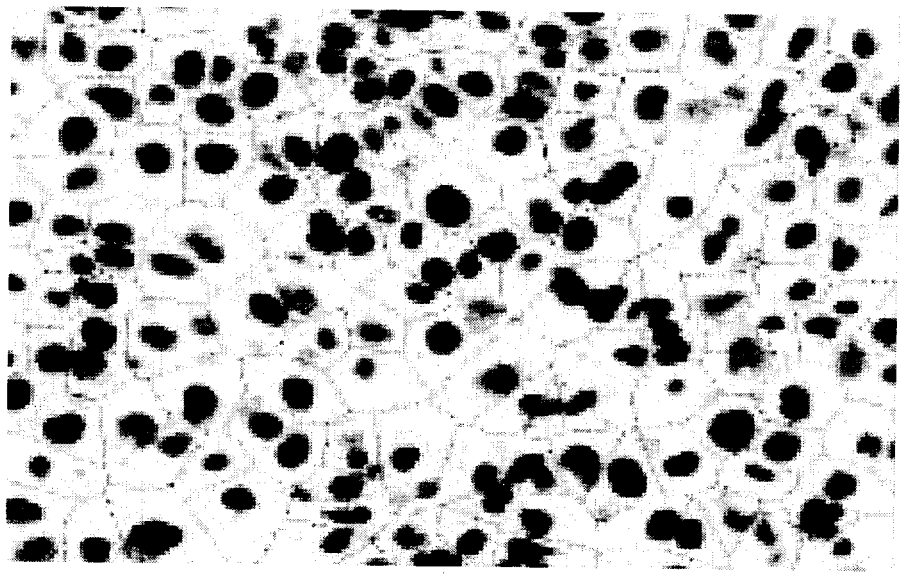
FIG. 4B is an example of a Voronoi neighbourhood.
Figure 4C:
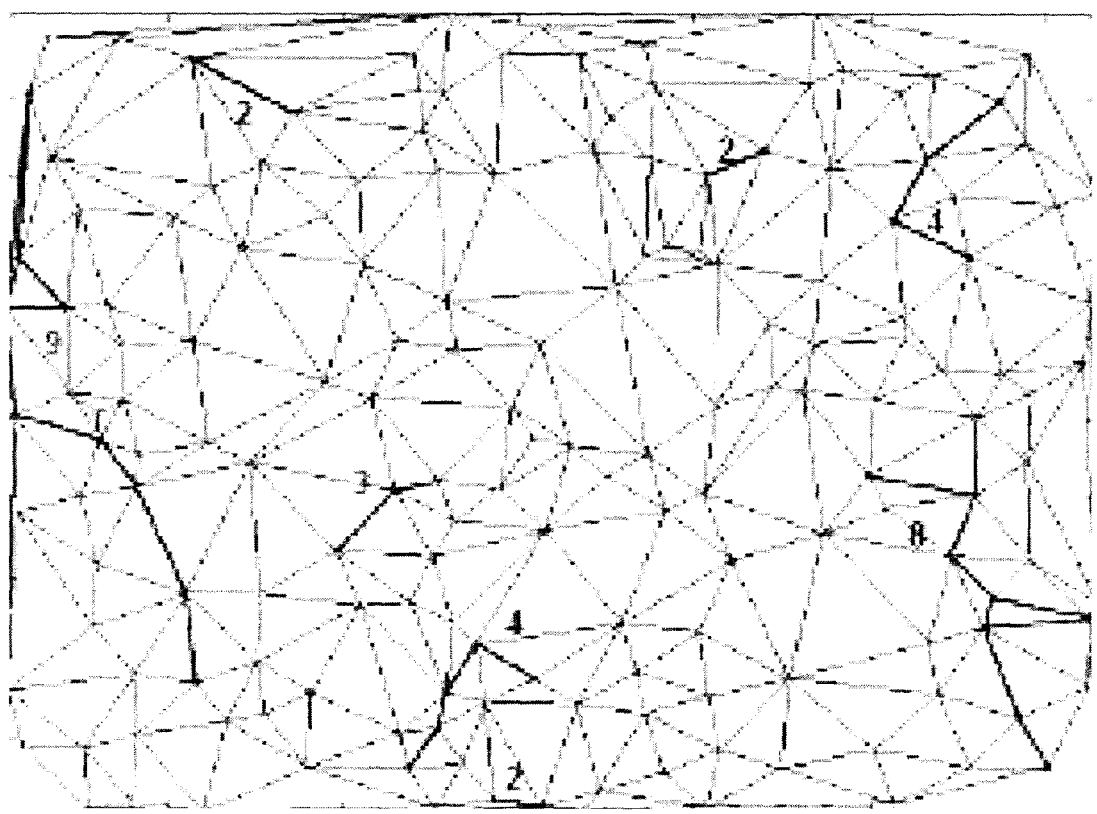
FIG. 4C is an example of a Delaunay graph applied to an image in which a number of cell nuclei have been identified.

FIG. 4A is an example of a Voronoi tessellation applied to an image in which a number of cell nuclei have been identified. FIG. 4B is an example of a Voronoi neighbourhood. FIG. 4C is an example of a Delaunay graph applied to an image in which a number of cell nuclei have been identified. In each case, the applied mathematical construct provides a basis for defining cell-to-cell associations. Either or both of these mathematical constructs can be performed on an individual field of view (FOV) or on an image made up of multiple FOVs that are stitched together.

The Voronoi tessellation may be applied as a basis for assessing the immediate and extended neighbourhood of a cell. A Voronoi tesselation may be developed by determining the center of gravity of each object (e.g. each nucleus). A Voronoi tesselation may be constructed by making a set $\{p\}$ of these center-of-gravity points and for each of the points, $p_i$, in $\{p\}$ defining a Voronoi cell V $\{p\}$ as the set of all points in the plane that are closer to $p_i$ than to all points other than $p_i$ in $\{p\}$. Constructing Voronoi tessellations is described, for example, in:

Haroske G, et al. *Cellular sociology of proliferating tumor cells in invasive ductal breast cancer* Anal Quant Cytol Histol 18(3):191-8, 1993; and Emily M, et al. *Spatial correlation of gene expression measures in tissue microarray core analysis* Journal of Theoretical Medicine 6(1):33-39, 2005.

Cells in a Voronoi tessellation can be considered neighbors when they share a common polygon edge. Since cells are usually surrounded by other individuals on all sides, Voronoi neighbourhoods tend to resemble oval regions. By increasing the number of layers to be included in the neighbourhood (i.e. by including up to $n^{th}$-nearest neighbors, where n=1, 2, 3, . . . ) one can define Voronoi neighbourhoods of different sizes surrounding any cell.

In some embodiments restrictions are placed on the area and distance of neighbors. For example, a threshold may be specified for the maximum physical distance separating two adjacent cells. The threshold may be fixed or computed on a case-by-case basis. For example, the threshold may comprise a suitable multiple of the average cell-to-cell spacing for a tissue sample.

Figure 4D:
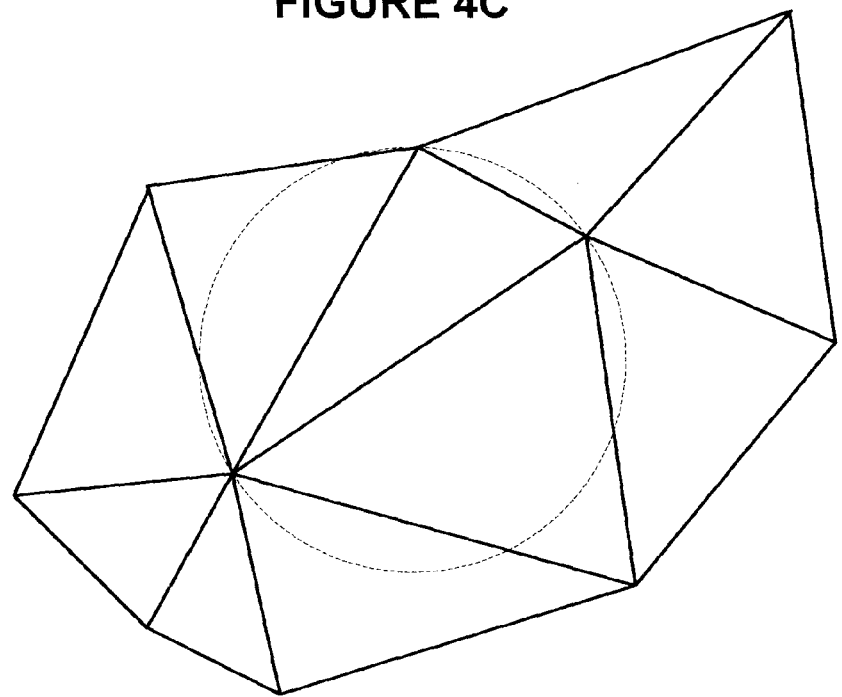
FIG. 4D shows an outcircle in a Delaunay graph.

As shown in FIG. 4C, a Delaunay graph or Delaunay triangulation comprises cell-to-cell connections. Note that common edges of a Voronoi tesselation can also be considered to be cell-to-cell connections. The Delaunay connections can be straight lines that are laid out to connect closest cell nuclei such that no other cell nuclei are located within the outcircle of each triangle formed. The outcircle of a triangle is a circle passing through the three apexes of the triangle. The lines may join suitable points on adjacent nuclei. For example, the lines may join the centroid of each nucleus to adjacent nuclei. FIG. 4D shows a Delaunay triangulation for a sample set of data points and an outcircle for one triangle that connects three of the data points.

A Delaunay graph may be used to define spatial relationships between cells that share one or more traits of interest. For example, a number of cells that share a trait of interest may be considered to form a group if a path made up of a continuous chain of cell-to-cell connections, each connection connecting two cells that share the trait of interest, extends between each pair of the cells in the group. With this definition, a group may be of virtually any size depending on the distribution of cells having the trait in question. Such groups are not limited to groups of $n^{th}$-nearest neighbors. FIG. 4C shows several groups of cells having biomarkers indicative of a trait. The members of each group are linked by the cell-to-cell connections. The groups can have essentially arbitrary shapes.

In block 38 characters are computed. In some embodiments, a single character is computed for an entire group of cells identified in block 36. In example embodiments, the characters are scores. In some embodiments, characters are computed on a cell-by cell basis and take into account the spatial position of a current cell in the group of cells to which the current cell belongs. In embodiments in which truncated cells are identified as such, determining a score or other character for a group of cells may take into account the presence and the large uncertainty with respect to the attributes of such truncated cells. At block 40 the characters computed in block 38 are applied.

A score can be determined for a Voronoi neighbourhood in various ways. For example the score may be, or may be based upon the percentage of cells exhibiting a specific trait of interest within a specified Voronoi neighbourhood. This can provide information about whether the neighbourhood includes many or few cells having the trait in question whether or not those cells are connected to one another. This can be beneficial since sectioning artefacts can split clonal connectivity from above or below the section imaged. In some embodiments different layers are weighted differently. Since Voronoi neighbourhoods tend to be generally oval or circular in shape, scoring based on Voronoi neighbourhoods tends to preferentially score oval or circular tumour subpopulations.

Consider, for example, the Voronoi neighbourhood shown in FIG. 4A. FISH positive cells are identified by circles. For the cell at the center of the neighbourhood, the first layer has two FISH positive cells out of eight $1^{st}$ neighbors. The second layer has four FISH positive cells out of fifteen $2^{nd}$ neighbors. The third layer has 5 FISH positive cells out of 22 $3^{rd}$ neighbors. A score may be constructed for this central cell, for example, by adding together the proportion of FISH positive cells in each layer. In this case, $2/8+4/15+5/22 \approx 0.74$. Other scoring formulae may be applied in the alternative.

In some embodiments, the size of Voronoi neighborhood used to determine a score for a current cell is a function of the degree to which the current cell has the trait in question. If the current cell has the trait very strongly then a smaller Voronoi neighborhood may be chosen whereas, if the current cell has the trait more weakly then a larger Voronoi neighborhood may be used to determine a score or other character for the current cell. Such embodiments can be effectively applied, for example, where the trait of interest is amplification of a gene. A cell may show one or more extra copies of the gene. The size of the Voronoi neighborhood may be established based at least in part on the number of extra copies of the gene in the current cell. As another example, the trait may comprise the degree to which a nucleus or cell is stained with a particular stain. In this case, the size of the Voronoi neighborhood may be established based at least in part on the density of staining for the current cell.

The Delaunay graph can be used as a basis for a score or other measure of connectivity. In some embodiments, cells having a specific trait being investigated are identified and a score is generated for each clonal neighbourhood based at least in part on one or more of:
- the number of cells having the trait that are connected by an uninterrupted chain of Delaunay cell-to-cell connections.
- the length of a longest uninterrupted chain of Delaunay cell-to-cell connections which each connect two cells having the trait.
- the number of cells having the trait that are connected to one another by Delaunay cell-to-cell connections which each connect two cells having the trait.
- the sum of scores for all cells in a Delaunay group.
- a combination of the above.
- etc.

Such Delaunay-based scores assess connectivity without any preference for clonal groups having particular shapes. Many such Dalaunay-based scores can be computed with relatively small computational overhead.

In some embodiments the concept of a group based on a Dalaunay graph is extended to permit cells to be grouped together even if a chain of cell-to-cell connections linking the cells passes through some cells that do not have the trait for which the group is defined. In such embodiments:
- the length of any gaps may be limited (i.e. each pair of cells in a group are linked by some chain of cell-to-cell connections which does not pass through any section having more than q cells in a row that do not have the trait, where q is some non-negative integer);
- the number of gaps may be limited (i.e. each pair of cells in a group are linked by some chain of cell-to-cell connections which has no more than r gaps in which the chain passes through one or more cells that do not have the trait, where r is some non-negative integer);
- the total number of cells that do not have the trait in any gaps may be limited (i.e. each pair of cells in a group are cells that have the trait that are linked by some chain of cell-to-cell connections which passes through no more than s cells that do not have the trait, where s is some non-negative integer);
- the length of gaps in terms of physical dimensions may be limited to permit gaps only up to some threshold length.
- the length of gaps may be dependent upon the biomarker signal strength of cells on one or both sides of the gap (for example, where cells in groups on one or both sides of a gap have a strong biomarker signal then the groups may e joined across a wider gap than in cases where the cells have weaker biomarker signals).
- some combination of two or more of the above;
- etc.

Allowing groups to include chains of cells having the trait that include some gaps permits enhanced recognition of larger-scale structures in tissues in which a clonal population of interest is intermixed with other cells or in which some cells and/or cell nuclei are affected by truncation artefacts.

One way to determine whether a first group of cells having a trait should be merged with another cell or group of cells having the trait is to take Voronoi neighborhoods of an appropriate order for cells in the first group and to determine whether any of those Voronoi neighborhoods include cells of other groups of cells having the trait. In some embodiments, the Voronoi neighborhoods may have sizes dependent on the biomarker signals strength (e.g. number of amplifications, density of staining etc.) of the cell on which the group is centered. Higher signal strength may correspond to larger Voronoi neighborhoods being used to determine if the current group should be merged with any other groups.

In some embodiments, cells identified as being truncated nuclei are treated differently from other nuclei when determining whether a group can be extended across a gap. For example:
- Gaps may be permitted if the gaps contain nuclei recognized as truncated nuclei. In some embodiments, gaps are permitted only if all of the nuclei in a gap are recognized as truncated nuclei.
- In some embodiments, nuclei identified as likely being affected by truncation artefacts do not count toward the length of a gap. In some embodiments, such nuclei are also excluded from a group for the purpose of computing a character for the group. In some embodiments, nuclei identified as truncated nuclei are treated as if they had characteristics as determined by a statistical analysis of surrounding nuclei for the purpose of computing the character of a group.

Figure 5A:
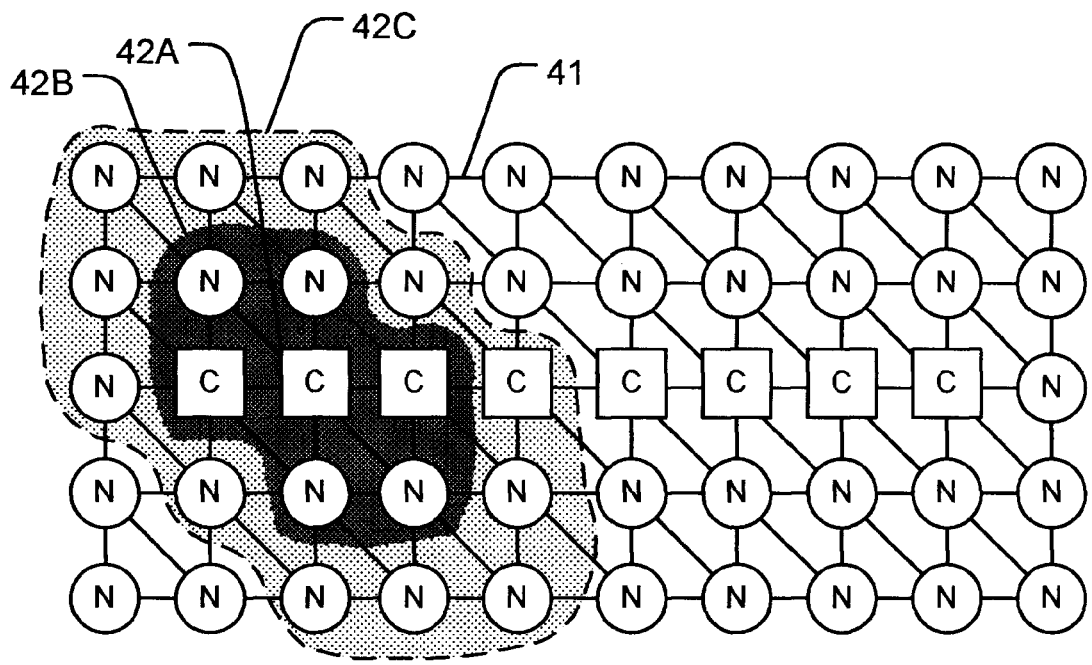
FIG. 5A shows schematically a Voronoi neighborhood of a cell in a tissue specimen.

FIGS. 5A through 5D illustrate the application of example methods to grouping cell nuclei. In these Figures, cell nuclei are represented as being located on a spatially-regular grid. This is never the case in natural tissues but is convenient for purposes of illustration and explanation. FIG. 5A shows a portion of an image of a tissue comprising a number of normal cells labelled "N" and a number of cells having a mutation of interest that are labelled "C". The cells have previously been identified as belonging to one of these two groups based on one or more biomarkers.

FIG. 5A includes cell-to-cell connections 41, such as Delaunay connections, or common edges in a Voronoi tesselation that join adjacent cells. A Voronoi neighbourhood centered on a cell-of-interest 42A has a layer of first-nearest neighbors 42B and a layer of second-nearest neighbors 42C. Similar Voronoi neighbourhoods may be established for any cell of FIG. 5A. It can be seen that the cell of interest has the mutation. Of the six first-nearest neighbors, only two have the mutation. Of the 12 second-nearest neighbors only one has the mutation. Scores computed for the Voronoi neighborhood of the cells depicted in FIG. 5A may be relatively low even though there is a clear group of invading mutated cells.

Figure 5B:
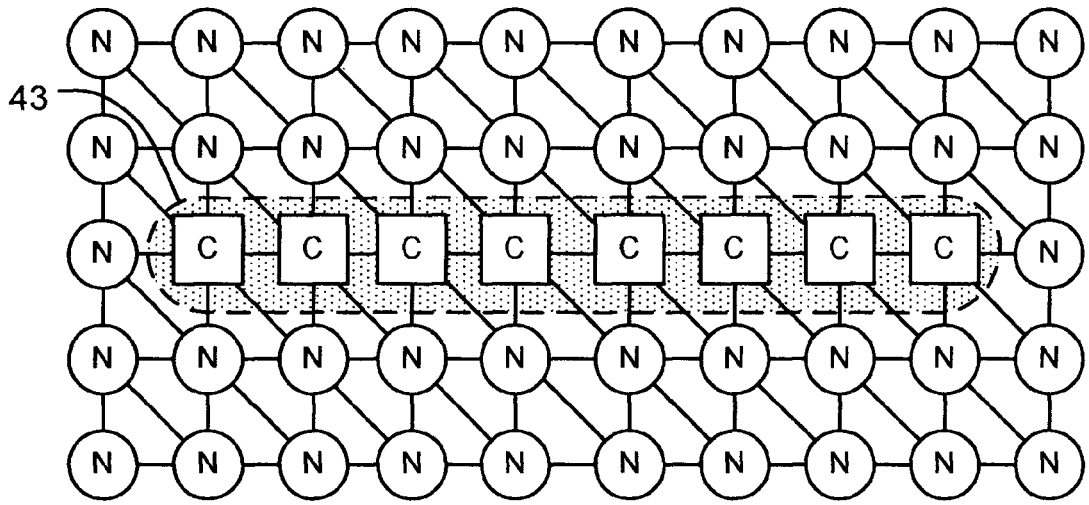
FIGS. 5B, 5C and 5D illustrate groups of cells established on the basis of connectivity and characteristics of the cells.

FIG. 5B illustrates the same tissue sample as is shown in FIG. 5A. In FIG. 5B, however, cells identified as having the mutation have been grouped together based on their connectivity through connections 41. In the illustrated case, all of the mutated cells, labeled "C" are connected by a continuous chain of connections 41. A score or other character for group 43 or its member cells can provide a strong indication of the presence of a clonal group of mutated cells C.

Figure 5C:
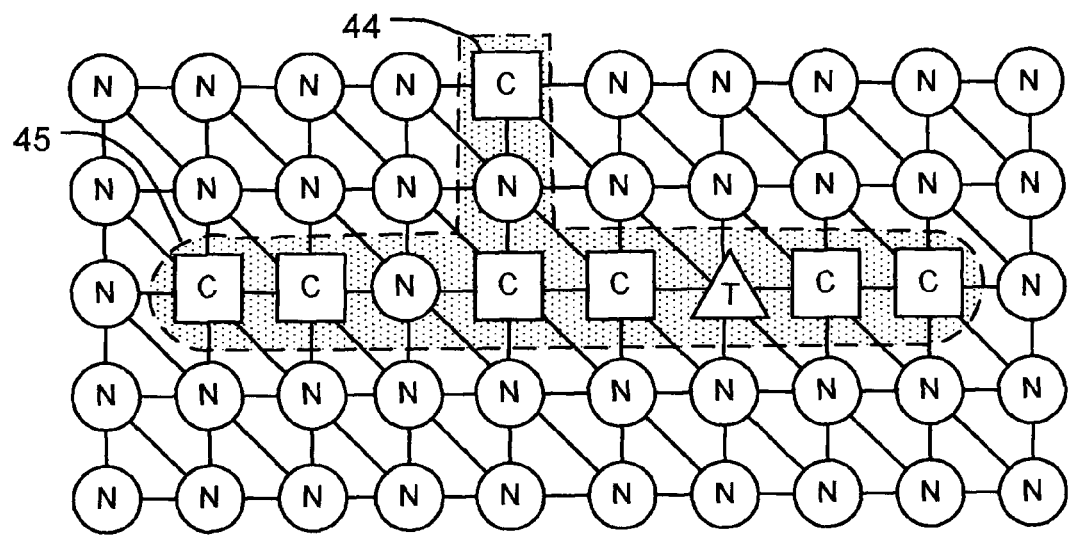

FIG. 5C illustrates a tissue sample that is similar to that of FIGS. 5A and 5B except that the chain of mutated cells is interrupted by one normal cell N and one cell, labeled "T", that has been identified as being truncated. Also, another mutated cell 44 is present nearby. These normal and truncated cells are at locations such that they create gaps in the chain of mutated cells. The gaps each bridge over one cell not belonging to the set of mutated cells C. Where an algorithm allows cells to be grouped despite such gaps, as described above, then, in this example, all of the mutated cells shown are grouped into a single group 45. A score or other character for group 45 or its member cells can provide a strong indication of the presence of a clonal group of mutated cells C.

Figure 5D:
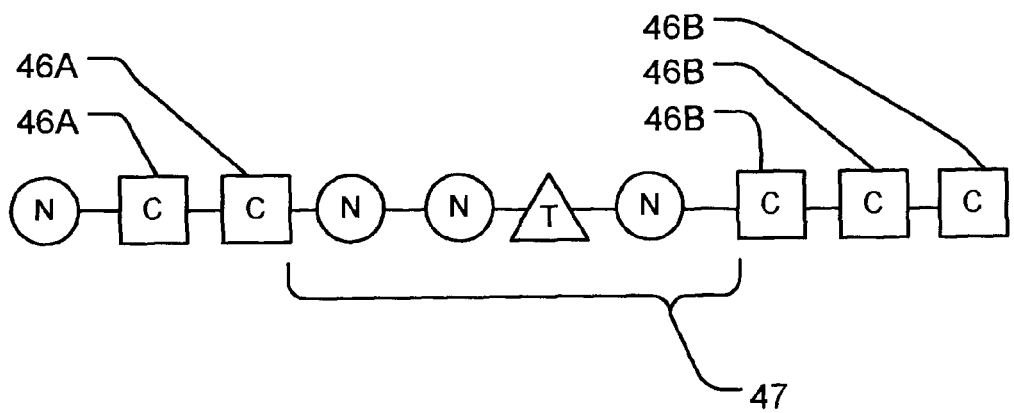

FIG. 5D illustrates a chain of cells which includes a number of mutated cells 46A and 46B separated by a gap 47. Whether cells 46A and 46B can be all combined into a single group will depend upon the length of gap that can be bridged. In the illustrated situation, gap 47 includes four cells that are not in the selected set of mutated cells. If the algorithm being applied will only group together cells that are separated by a gap of three or fewer non-member cells then cells 46A and 46B would normally not be grouped together as a single group. One cell in gap 47 has been identified as being truncated. In embodiments which ignore truncated cells in determining gap length then cells 46A and 46B would be grouped together if the algorithm permits gaps of three or fewer non-member cells.

Methods as described herein which group together similar cells even in cases where the cells are separated by gaps of up to a defined size can enable definition of clonal populations over and around infiltrating normal cells as well as providing robustness that minimizes artefacts caused by lost FISH signals due to sectioning artefacts and spurious signal gains due to segmentation errors.

In some embodiments, cells are identified as being positive for a trait of interest based on a method like that of FIG. 10 which considers biomarkers for a current cell of interest and can also consider biomarkers for neighboring cells. The positive cells are then grouped into Delaunay groups, for example by one of the methods described above. Then the cells in each Delaunay group are individually examined to determine if their biomarkers satisfy a rule for being positive for the trait of interest. If at least a set threshold proportion of the cells in a group are determined to be positive for the trait then the group may be identified as being positive for the trait. Methods of this type allow the probability that each individual cell possesses the trait of interest to be iteratively updated. This is of value, for example in cases where FISH is used to study a tissue section for which a significant fraction of the cells suffer from truncation artefacts which cause some FISH spots to be missing that would otherwise be present.

It can be appreciated that the techniques described herein may be applied to identifying clonal populations of cells. 'Clonal population' may be defined as a group of spatially adjacent or closely spatially associated cells having attributes that are similar within some quantifiable set of measures. A clonal population may, for example, incorporate a defined level of non-clonal cell infiltrates.

The attributes that a clonal population may share can be attributes like, for example, number of FISH spots for a specific collection of genetic loci, expression levels for one or more IHC markers, etc. Analysis of the multicolor FISH signal (or other collections of attributes) solely within a clonal population enables an aggregated scoring that can provide results that are more relevant than those provided by standard methods of tissue scoring.

It is possible but not mandatory that the same attributes be applied for both identifying a group of cells and scoring the group of cells. In some embodiments, clonal populations are identified with reference to one set of biomarkers and scoring is performed according to a second set of biomarkers. The second set of biomarkers may be any of:
  the same as;
  different from but overlapping with; and
  different from and not overlapping with
the first set of biomarkers.

In some embodiments, scoring comprises weighting individual cells based upon a measure of distance from a current cell of interest. The measure of distance may, for example, comprise:
  the physical distance from the current cell of interest to the individual cell whose contribution is being weighted;
  the number of Delaunay cell-to-cell connections in the shortest path joining the current cell of interest to the individual cell whose contribution is being weighted;
  the Voronoi layer of the individual cell whose contribution is being weighted relative to the current cell of interest;
  etc.

In some embodiments, groups of similar cells are identified for the same image using two or more different mathematical constructs (e.g. both Voronoi neighborhoods and Delaunay triangulation). In such embodiments, measures may be computed based on both cell groupings. A result or results may be based upon some function of the separately-computed measures. The function may include a ratio or weighted ratio of the separately-computed measures.

In some embodiments, other mathematical constructs are used. For example, in some such embodiments an anatomical structure such as a basement membrane is identified in an image and the mathematical construct takes into account orientation relative to the anatomical structure. For example, the mathematical construct may tend to group together sets of similar cells that are spatially close together and are in a distribution that extends more-or-less perpendicular to a basement membrane in preference to grouping together similar cells that are spatially close together but are in a distribution that extends more-or-less parallel to the basement membrane.

To assess the ability of FISH and these mathematical definitions to identify known clonal clusters of cells (normal cells vs. cancer cells in tumour sections, cancer cells vs. mouse infiltrates in mouse xenograph tissues), a section of a mouse xenograft human squamous cell NSCLC tumour was treated with a solid tumour probe set from Abbott Laboratories. Abbott Park, Ill., U.S.A, called LAVysion™. The LAVysion probe set includes a mixture of four directly labelled FISH probes for DNA sequences that are commonly amplified in lung cancers. The locus-specific (LSI) EGFR (epidermal growth factor receptor) gene probe is labeled in Spectrum-Red and covers a 300 kb region that contains the entire EGFR gene (7p12). The approximately 750 kb Spectrum-Gold labeled LSI C-MYC probe, contains the entire C-MYC gene (8q24.12-q24.13). The LAVysion multi-color probe set also contains an approximately 450 kb Spectrum-Green sequence labeled LSI D5S23, D5S271 (5p15.2) and a centromere enumeration probe (CEP) for chromosome 6 labeled in Spectrum-Aqua. The CEP 6 probe hybridizes to the alpha satellite DNA region located at the centromere of chromosome 6. Images of the sectioned tissues were acquired, segmented, and reformatted into MATLAB™.

In MATLAB, FISH spots were counted and Delaunay architectural scores were computed. In this example, areas of double deletion in all channels were identified. These areas, which lack any signal, are likely mouse infiltrates from the mouse xenograft (since double deletion in all 4 channels is highly unlikely). The techniques described herein may equally be applied to other traits such as single genetic deletions, single genetic amplifications and multiple genetic amplifications.

Figure 6:
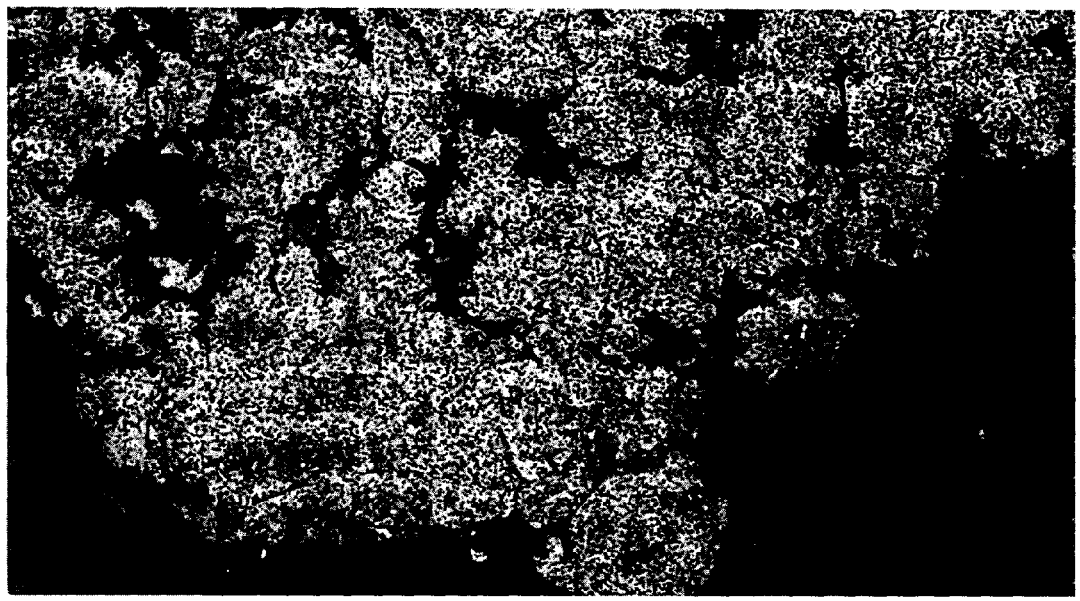
FIG. 6 is an image of a section through a mouse xenograph.
Figure 7:
FIG. 7 is the image of FIG. 6 with areas corresponding to neighbourhoods of cells with amplified FISH signals highlighted.
Figure 7B:
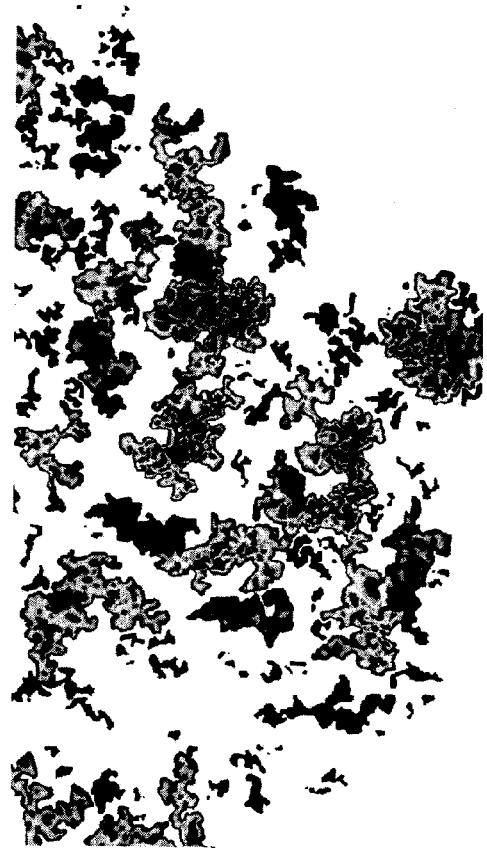
FIGS. 7A and 7B are respectively a view similar to FIG. 6 and an overlay containing highlighting representing neighborhood scores.
Figure 7A:
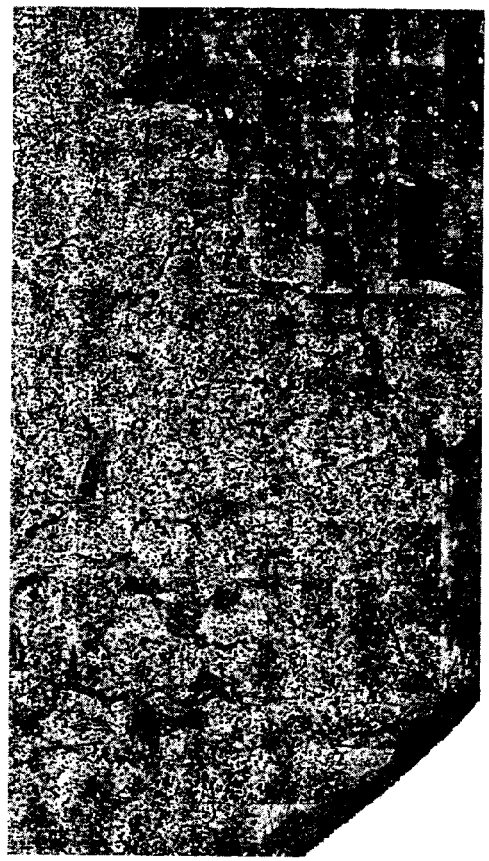
Figure 8B:
FIGS. 8A and 8B are respectively a further magnified view of an area containing high-connectivity cells having amplified FISH values and an overlay containing highlighting representing neighborhood scores.
Figure 8B:
Figure 8A:

FIGS. 6 to 8 demonstrate an application of the invention using FISH biomarkers to differentiate and delineate clonal populations based upon a double deletion. FIG. 6 is a composite of many micrographs of tissue samples of a mouse-human xenograft lung tumour prepared with a counterstain targeting cell nuclei. The image is partitioned into light and dark grey areas which denote whether the system classified that region as human tumour or non-human tumour (as determined by doubly deleted FISH spots in each of the 4 channels), respectively. The same xenograft tissue was also examined for regions with abnormal amplified signal for any of the 4 probes. This method identified nearly every region not belonging to double deleted (ie mouse infiltrate) cells as abnormal (see FIG. 7). This makes sense as the entire human part of the xenograft should be tumour and thus display an abnormal signal. Any areas not included may be a single deletion (not included), a normal signal due to truncation or the result of rejection based on quality of segmentation or background signal.

FIGS. 7 and 8 are examples of highlighting areas in an image based on the degree of connectivity of cells showing a trait with other cells also showing the trait. In FIGS. 7 and 8, red contours indicate areas of high connectivity with other amplified cells, ie other cells with at least one other channel amplified while the blue contours indicate areas with above-normal tissue scores.

Figure 9:
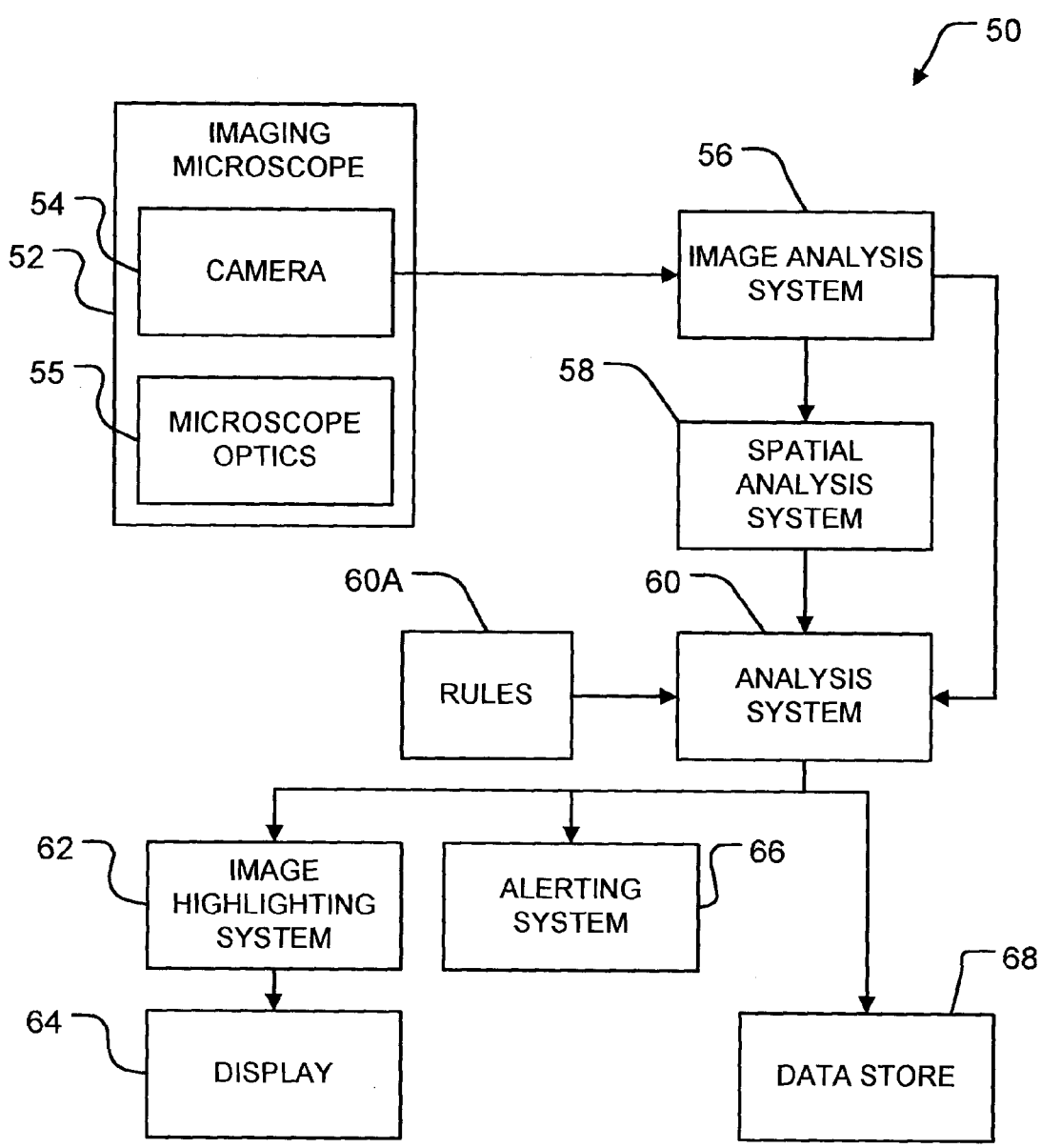
FIG. 9 is a block diagram of apparatus according to an example embodiment.

FIG. 9 illustrates apparatus 50 according to an example embodiment of the invention. Apparatus 50 comprises an imaging microscope 52. Any suitable imaging microscope may be provided. For example, imaging microscope 52 may comprise a Zeiss Z1™ microscope equipped with a suitable camera. In a prototype embodiment, microscope 52 comprises a microscope which makes up part of the Metasystems™ FISH system. Imaging microscope 52 includes a camera 54. In the prototype embodiment the camera generates images of 1280×1024 pixels with a pixel size of 6.7 µm square.

Microscope 52 includes microscope optics 55 which include illumination systems suitable for the imaging modality(ies) to be used. In the prototype embodiment, the illumination system comprises a light engine is based on a Texas Instruments™ digital micro-mirror device, or 'DMD' controlled by a controller that permits the DMD to be controlled to output arbitrary spectral profiles. Illumination systems of this type are described in:

MacKinnon N, et al. *Spectrally programmable light engine for in vitro or in vivo molecular imaging and spectroscopy*, Appl Opt vol. 44, pp. 2033-2040, Apr. 10, 2005; and MacKinnon N, et al. *Hyperspectral imaging and spectral unmixing of stained tissue sections using a spectrally programmable light engine*, Proc. SPIE Vol. 6441, March 2007.

Such Spectrally Programmable Light Engine ('SPLE') illumination systems are commercially available from Onelight Corp. of Vancouver, Canada.

Data from camera 54 is passed to an image analysis system 56. Image analysis system 56 may comprise, for example, a programmed data processor which processes image data from camera 54 by segmenting the images to identify structures such as cell nuclei and by recognizing biomarkers. Output from the image analysis system 56 is presented to a spatial analysis system 58. Spatial analysis system 58 identifies spatial relationships between cell nuclei or other structures identified by image analysis system 56. For example, spatial analysis system 58 may compute a Voronoi tesselation and/or a Delaunay triangulation for cell nuclei identified by image analysis system 56.

An analysis system 60 groups cell nuclei based upon output from spatial analysis system 58 and biomarkers identified by image processing system 56 and computes scores or other results for the grouped cell nuclei. The grouping is performed according to rules 60A.

Output from analysis system 60 is provided to an image highlighting system 62 which may produce one or more of:
  highlighted images;
  contour maps showing variation of a result determined by analysis system 60 over the area of the image;
  false color images;
  magnified views of areas of an image selected with reference to results generated by output analysis system 60;
  etc.
Highlighted imaged produced by image highlighting system 62 are displayed on a display 64.

An alerting system 66 determines whether scores or other output from analysis system 60 indicates that an alert ought to be generated. The alert may, for example: request human inspection of images or selected parts thereof; request follow up tests or physician intervention; or the like. In some embodiments alerts comprise e-mail messages or other electronic communications to one or more recipients (who may comprise humans and/or automated systems).

A data store 68 is provided to receive and store results from analysis system 60 and images.

Certain implementations of the invention comprise computer processors which execute software instructions which cause the processors to perform a method of the invention.

For example, one or more processors in a computer system may implement the methods of FIG. 1 or 2 or provide apparatus corresponding to one or more of blocks 56, 58, 60, 62 or 66 of apparatus 50 by executing software instructions in a program memory accessible to the processors. The invention may also be provided in the form of a program product. The program product may comprise any medium which carries a set of computer-readable signals comprising instructions which, when executed by a data processor, cause the data processor to execute a method of the invention. Program products according to the invention may be in any of a wide variety of forms. The program product may comprise, for example, physical media such as magnetic data storage media including floppy diskettes, hard disk drives, optical data storage media including CD ROMs, DVDs, or electronic data storage media including ROMs, flash RAM, or the like. The computer-readable signals on the program product may optionally be compressed or encrypted.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A method for automated determination of tissue characteristics, the method comprising:
    obtaining an image of a tissue sample, the image depicting cell nuclei and corresponding biomarkers in the tissue sample; and,
    by a computer executing software instructions:
    processing the image to identify in the image: the cell nuclei, corresponding biomarkers associated with the cell nuclei, and spatially-connected groups of the cell nuclei;
    computing characters of the spatially-connected groups of cell nuclei; and,
    based at least in part on the computed characters, highlighting regions corresponding to the spatially-connected groups of cell nuclei;
wherein identifying the spatially-connected groups of the cell nuclei in the image comprises:
    identifying a selected set of the cell nuclei for which the corresponding biomarkers satisfy a selection criterion;
    establishing a network of cell-to-cell connections connecting adjacent ones of the cell nuclei; and
    identifying a group of the cell nuclei of the selected set that are all interconnected by at least one chain of the cell-to-cell connections wherein: the at least one chain passes only through cells of the selected set except for in at least one gap in which the chain passes through from 1 to n consecutive cells that are not in the selected set and at least one pair of cells in the group is not interconnected by any chain of the cell-to-cell connections that passes only through cells of the selected set.

2. A method according to claim 1 wherein highlighting the regions comprises generating an overlay for the image comprising contours, the contours corresponding to values of the computed characters.

3. A method according to claim 1 wherein highlighting the regions comprises, automatically selecting based at least in part on the computed characters one or more areas within the image and preparing the selected areas for human review.

4. A method according to claim 3 wherein preparing the selected areas for human review comprises generating magnified views of the selected areas.

5. A method according to claim 4 wherein highlighting regions corresponding to the spatially-connected groups of cell nuclei comprises coloring regions corresponding to the spatially-connected groups of cell nuclei in the magnified views.

6. A method according to claim 1 wherein identifying a selected set of the cell nuclei for which the corresponding biomarkers satisfy a selection criterion comprises identifying cell nuclei associated with a specific set of FISH spots.

7. A method according to claim 1 wherein identifying a selected set of the cell nuclei for which the corresponding biomarkers satisfy a selection criterion comprises:
    identifying a neighborhood comprising a plurality of the cell nuclei that are neighbors of a selected one of the cell nuclei; and
    determining whether all of a specific set of biomarkers are present among the biomarkers associated with the cell nuclei of the neighborhood.

8. A method according to claim 7 further comprising determining whether, for each of the biomarkers of the specific set of biomarkers, at least a threshold proportion of the cells of the neighborhood are associated with the biomarker.

9. A method according to claim 1 wherein identifying a selected set of the cell nuclei for which the corresponding biomarkers satisfy a selection criterion comprises adding the current cell nucleus to the selected set:
    if a current cell nucleus is associated with all biomarkers of a specified set of biomarkers; and,
    if the current cell nucleus is not associated with all biomarkers of the specified set of biomarkers but, all of the specific set of biomarkers are present among the biomarkers associated with the cell nuclei of a neighborhood comprising a plurality of the cell nuclei that are neighbors of the current cell nucleus.

10. A method according to claim 9 wherein the neighborhood comprises a Voronoi neighborhood of the current cell nucleus.

11. A method according to claim 1 wherein identifying a selected set of the cell nuclei for which the corresponding biomarkers satisfy a selection criterion comprises adding the current cell nucleus to the selected set:
    if the biomarkers associated with a current cell nucleus satisfy a first rule; and,
    if the biomarkers associated with the current cell nucleus do not satisfy the first rule but the biomarkers associated with the cell nuclei of a neighborhood comprising a plurality of the cell nuclei that are neighbors of the current cell nucleus satisfy a second rule.

12. A method for automated determination of tissue characteristics, the method comprising:
    obtaining an image of a tissue sample, the image depicting cell nuclei and corresponding biomarkers in the tissue sample; and,
    by a computer executing software instructions:

processing the image to identify in the image: the cell nuclei, corresponding biomarkers associated with the cell nuclei, and spatially-connected groups of the cell nuclei;
computing characters of the spatially-connected groups of cell nuclei; and,
based at least in part on the computed characters, highlighting regions corresponding to the spatially-connected groups of cell nuclei;
wherein identifying the spatially-connected groups of the cell nuclei in the image comprises:
identifying a selected set of the cell nuclei for which the corresponding biomarkers satisfy a selection criterion;
establishing a network of cell-to-cell connections connecting adjacent ones of the cell nuclei;
identifying first and second disjoint groups of the cell nuclei of the selected set, each of the first and second groups comprising a plurality of the cell nuclei of the selected set that are interconnected by at least one chain of the cell-to-cell connections; and,
determining whether a gap comprising one or more cell nuclei that are not members of either the first or second groups satisfies a rule and, if so, uniting the first and second groups.

13. A method according to claim 12 wherein the rule comprises determining one or more of:
whether a number of cell nuclei in the gap is smaller than a first threshold; and
whether a physical length of the gap is smaller than a second threshold.

14. A method according to claim 12 wherein determining whether the gap satisfies the rule comprises determining whether a cell nucleus of the second group is in a Voronoi neighborhood of a cell nucleus of the first group.

15. A method according to claim 12 wherein the character is a function at least in part of the number of members in each spatially-connected group.

16. A method according to claim 12 wherein the character is a function of the spatial relationship of a cell nucleus to other members of the spatially-connected group to which the cell nucleus belongs.

17. A method according to claim 12 comprising performing an action in response to the computed characters wherein the action comprises selecting one or more areas within the image to be: enlarged, saved for future analysis, subjected to further automated analysis, or displayed.

18. A method according to claim 12 wherein the biomarkers comprise multicolor FISH spots.

19. A method for automated determination of tissue characteristics, the method comprising:
obtaining an image of a tissue sample, the image depicting cell nuclei and corresponding biomarkers in the tissue sample; and,
by a computer executing software instructions:
processing the image to identify the cell nuclei and corresponding biomarkers in the image and to identify spatially-connected groups of the cell nuclei in the image; and
computing characters of the spatially-connected groups of cell nuclei;
wherein identifying spatially-connected groups of the cell nuclei in the image comprises:
identifying a selected set of the cell nuclei for which the corresponding biomarkers satisfy a selection criterion;
establishing a network of cell-to-cell connections connecting adjacent ones of the cell nuclei; and
identifying a group of the cell nuclei of the selected set that are all interconnected by at least one chain of the cell-to-cell connections wherein: the at least one chain passes only through cells of the selected set except for in at least one gap in which the chain passes through from 1 to n consecutive cells that are not in the selected set and at least one pair of cells in the group is not interconnected by any chain of the cell-to-cell connections that passes only through cells of the selected set.

20. A method according to claim 19 wherein the biomarkers comprise FISH signals.

21. A method according to claim 20 comprising computing a character for the group of cells.

22. A method for automated determination of tissue characteristics, the method comprising:
obtaining an image of a tissue sample, the image depicting cell nuclei and corresponding biomarkers in the tissue sample;
processing the image to identify the cell nuclei and corresponding biomarkers in the image and establishing a network of cell-to-cell connections connecting adjacent ones of the cell nuclei;
identifying a selected set of the cell nuclei for which the corresponding biomarkers satisfy a selection criterion; and,
identifying at least one spatially-connected group of the cell nuclei in the selected set by:
finding first and second subsets of the spatially-connected group of the cell nuclei such that all of the cells within each of the first and second subsets are connected by some chain of the cell-to-cell connections that does not connect to any cell not in the subset;
determining that a gap separating a first cell in the first subset from a second cell in the second subset has a size not exceeding a threshold;
combining the first and second subsets into a group; and
identifying a group of the cell nuclei of the selected set that are all interconnected by at least one chain of the cell-to-cell connections wherein: the at least one chain passes only through cells of the selected set except for in at least one gap in which the chain passes through from 1 to n consecutive cells that are not in the selected set and at least one pair of cells in the group is not interconnected by any chain of the cell-to-cell connections that passes only through cells of the selected set; and,
computing a character for the group of cells.

23. A method according to claim 22 wherein the character is based at least in part on a length of the at least one chain in the group of cells.

24. A method according to claim 22 wherein the character is based at least in part on FISH scores for cells in the group.

25. A method according to claim 22 wherein the character is based at least in part on distances between a current cell and the other cells in the group.

26. A method according to claim 25 wherein the distances are a number of the cell-to-cell connections in shortest chains connecting the current cell and the other cells in the group.

27. A method according to claim 22 wherein the cell-to-cell connections comprise connections of a Delaunay triangulation.

28. A method according to claim 22 wherein the biomarkers comprise FISH spots.

* * * * *